US008586293B2

(12) United States Patent
Siegel

(10) Patent No.: US 8,586,293 B2
(45) Date of Patent: *Nov. 19, 2013

(54) COMPOSITIONS, METHODS AND KITS FOR DETECTION OF AN ANTIGEN ON A CELL AND IN A BIOLOGICAL MIXTURE

(75) Inventor: Donald L. Siegel, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 945 days.

This patent is subject to a terminal disclaimer.

(21) Appl. No.: 11/074,542

(22) Filed: Mar. 8, 2005

(65) Prior Publication Data

US 2005/0191622 A1 Sep. 1, 2005

Related U.S. Application Data

(63) Continuation of application No. PCT/US03/29231, filed on Sep. 18, 2003.

(60) Provisional application No. 60/411,693, filed on Sep. 18, 2002.

(51) Int. Cl.
*C12Q 1/70* (2006.01)

(52) U.S. Cl.
USPC ............. 435/5; 435/7.21; 435/7.25; 436/520; 436/521

(58) Field of Classification Search
None
See application file for complete search history.

(56) References Cited

U.S. PATENT DOCUMENTS

| | | | |
|---|---|---|---|
| 5,658,727 A | 8/1997 | Barbas et al. | |
| 5,691,132 A * | 11/1997 | Wollowitz et al. | 435/2 |
| 5,698,426 A | 12/1997 | Huse | |
| 5,770,356 A | 6/1998 | Light, II et al. | |
| 5,789,208 A | 8/1998 | Sharon | |
| 5,846,533 A * | 12/1998 | Prusiner et al. | 424/130.1 |
| 5,856,092 A * | 1/1999 | Dale et al. | 435/6 |
| 5,876,925 A | 3/1999 | Siegel | |
| 5,985,543 A * | 11/1999 | Siegel | 435/5 |
| 6,232,079 B1 * | 5/2001 | Wittwer et al. | 435/6 |
| 6,255,455 B1 | 7/2001 | Siegel | |
| 6,740,492 B2 * | 5/2004 | Merril | 435/6 |
| 2005/0136399 A1 * | 6/2005 | Siegel | 435/5 |

FOREIGN PATENT DOCUMENTS

| | | | | |
|---|---|---|---|---|
| WO | WO 97/29210 | * | 8/1997 | C12Q 1/68 |
| WO | WO9729210 | * | 8/1997 | C12Q 1/68 |
| WO | WO9740176 | * | 11/1997 | C12N 15/62 |

OTHER PUBLICATIONS

Watkins et al (2000) Tissue Antigens. 55:219-228.*
Griffin et al (1995) Blood. 86(12): 4430-4436.*
Hughes-Jones et al (1999) British Journal of Haimatology. 105: 811-816.*
Urbaniak (2002) Vox Sanguinis. 83 (Suppl 1): 293-297.*
Leddy et al (1994) Blood. 84 (2): 650-656.*
Kempf et al (2001) Molecular Biotechnology. 17: 97-108.*
Gupta et al (2001) Prep. Biochem. and Biotechnol. 31(2): 185-200.*
Persson et al (1991) PNAS. 88: 2432-2436.*
Elenitoba-Johnson et al. Multiplex PCR by multicolor fluorimetry and fluorescence melting curve analysis. Nat Med. Feb. 2001;7(2):249-53.*
Bussel et al. Platelets: New Understanding of Platelet Glycoproteins and Their Role in Disease. Hematology Am Soc Hematol Educ Program. 2000. p. 222-240.*
Bux. Molecular nature of granuloctye antigens. Transfus Clin Biol. 2001. 8: 242-7.*
Zhang et al. rotein quantification from complex protein mixtures using a proteomics methodology with single-cell resolution. PNAS. 2001. 98(10): 5497-5502.*
Chang et al., "Isolation of an IgG anti-B from a human Fab-phage display library", Transfusion 41:6-12 (2001).
Djojonegoro et al., "Bacteriophage Surface Display of an Immunoglobulin-binding Domain of *Staphylococcus aureus* Protein A", Bio/Technology 12:169-172 (1994).
Hansen et al., "Identification of immunogenic antigens using a phage-displayed cDNA library from an invasive ductal breast carcinoma tumour", Int. J. Oncol. 19:1303-1309 (2001).
Russell et al., "Retroviral vectors displaying functional antibody fragments", Nucl. Acids Res. 21:1081-1085 (1993).
Siegel et al., "Isolation of cell surface-specific human monoclonal antibodies using phage display and magnetically-activated cell sorting: application in immunohematology", J. Immunol. Meth. 206:73-85 (1997).
Siegel, "Research and Clinical Applications of Antibody Phage Display in Transfusion Medicine", Transfusion Med. Rev. 15:35-52 (2001).
Sternberg et al., "Display of peptides and proteins on the surface of bacteriphage λ", Proc. Natl. Acad. Sci. U.S.A. 92:1609-1613 (1995).
Zhang et al., "Protein quantification from complex protein mixtures using a proteomics methodology with single-cell resolution", Proc. Natl. Acad. Sci. U.S.A. 98:5497-5502 (2001).
Miescher et al., 2000 Brit. J. Haematol 111:157-166.

* cited by examiner

*Primary Examiner* — Michelle S Horning
(74) *Attorney, Agent, or Firm* — Riverside Law LLP

(57) ABSTRACT

The present invention relates to novel methods for detecting a member of a known binding pair in a sample, including a cell, where one member of the pair (termed the "receptor") is expressed by a bacteriophage, which phage is then used to detect the presence of the other member of the pair (termed the "ligand" or "target"). Rather than detecting the binding of the phage using antibody-based technology, the present invention relates to detecting the nucleic acid associated with the phage. In one aspect, the invention relates to identifying an antigen-bearing moiety (e.g., a red blood cell antigen) of interest present on a cell, e.g., a red blood cell, using antibody-displaying bacteriophage, as well as detecting anti-red blood cell auto- or alloantibodies and/or complement in a sample, using antiglobulin reagent-displaying bacteriophage and detecting a nucleic acid associated with the phage.

28 Claims, 4 Drawing Sheets

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial
<220> FEATURE:
```

```
<223> OTHER INFORMATION: forward primer "5-prime LC"

<400> SEQUENCE: 1
aagacagcta tcgcgattg                                                    19

<210> SEQ ID NO 2
<211> LENGTH: 24
<212> TYPE: DNA
<213> ORGANISM: Artificial
<220> FEATURE:
<223> OTHER INFORMATION: reverse primer "GBACK"

<400> SEQUENCE: 2 gccccttat tagcgtttgc catc                                               24

<210> SEQ ID NO 3
<211> LENGTH: 142
<212> TYPE: DNA
<213> ORGANISM: Artificial
<220> FEATURE:
<223> OTHER INFORMATION: B140

<400> SEQUENCE: 3
tgctatgtca cttccccttg gttctctcat ctggcctggt gcaataggcc ctgcatgcac       60
tggatgcact ctatcccatt ctgcagcttc ctcattgatg gtctctttta acatttgcat      120
ggctgcttga tgtcccccca ct                                              142

<210> SEQ ID NO 4
<211> LENGTH: 142
<212> TYPE: DNA
<213> ORGANISM: Artificial
<220> FEATURE:
<223> OTHER INFORMATION: D140

<400> SEQUENCE: 4
tgctatgtca cttccccttg gttctctcat ctggcctggt gcaataggcc ctgcatgcac       60
tggatgcact ctgttttacc tcattatcct tctgccagcg ctagctttta acatttgcat      120
ggctgcttga tgtcccccca ct                                              142

<210> SEQ ID NO 5
<211> LENGTH: 27
<212> TYPE: DNA
<213> ORGANISM: Artificial
<220> FEATURE:
<223> OTHER INFORMATION: forward PCR primer "PCR-F"

<400> SEQUENCE: 5
tgctatgtca cttccccttg gttctct                                           27

<210> SEQ ID NO 6
<211> LENGTH: 30
<212> TYPE: DNA
<213> ORGANISM: Artificial
<220> FEATURE:
<223> OTHER INFORMATION: reverse PCR primer "PCR-R"

<400> SEQUENCE: 6
agtgggggga catcaagcag ccatgcaaat                                        30

<210> SEQ ID NO 7
<211> LENGTH: 45
<212> TYPE: DNA
<213> ORGANISM: Artificial
<220> FEATURE:
```

```
<223> OTHER INFORMATION: B-Beacon

<400> SEQUENCE: 7
gcgagcatcc cattctgcag cttcctcatt gatggtctcg ctcgc         45

<210> SEQ ID NO 8
<211> LENGTH: 45
<212> TYPE: DNA
<213> ORGANISM: Artificial
<220> FEATURE:
<223> OTHER INFORMATION: D-Beacon

<400> SEQUENCE: 8
gcgagcgttt tacctcatta tccttctgcc agcgctagcg ctcgc         45

<210> SEQ ID NO 9
<211> LENGTH: 33
<212> TYPE: DNA
<213> ORGANISM: Artificial
<220> FEATURE:
<223> OTHER INFORMATION: B-oligo

<400> SEQUENCE: 9
atcccattct gcagcttcct cattgatggt ctc                      33

<210> SEQ ID NO 10
<211> LENGTH: 33
<212> TYPE: DNA
<213> ORGANISM: Artificial
<220> FEATURE:
<223> OTHER INFORMATION: D-oligo

<400> SEQUENCE: 10
gttttacctc attatccttc tgccagcgct agc                      33
```

COMPOSITIONS, METHODS AND KITS FOR DETECTION OF AN ANTIGEN ON A CELL AND IN A BIOLOGICAL MIXTURE

CROSS-REFERENCE TO RELATED APPLICATIONS

The present application is a continuation of International Patent Application No. PCT/US03/29231, filed on Sep. 18, 2003, which is entitled to priority under 35 U.S.C. §119(e), to U.S. Provisional Application No. 60/411,693, filed on Sep. 18, 2002, each of which application is hereby incorporated herein by reference in its entirety.

BACKGROUND OF THE INVENTION

Each year in the United States alone, hundreds of millions of red blood cell (RBC) antigen typings are performed on donated units of blood and the patients that are to receive them. In addition, equivalent numbers of patient antisera are screened for the presence of pre-existing anti-RBC antibodies, the specificities of which must be identified prior to the selection of compatible blood. The technology used in blood banks for doing these tests is essentially the same as the one demonstrated by Landsteiner over 100 years ago—the agglutination of RBCs by an appropriate antisera. Assay systems of this type are labor intensive and typically require teams of highly-trained medical technologists manually shaking test tubes over magnifying mirrors and assessing agglutination patterns by eye. Consequently, blood banks require significantly more bench technologists per test than any other type of clinical laboratory, as reflected in the 10- to 100-fold greater cost per test for the transfusion laboratory than those for other areas of laboratory medicine. In addition, blood donation facilities, blood banks, and hospital transfusion services across the country are facing a growing shortage of skilled staff to perform such tests due to the lack of qualified and interested candidates. This is particularly concerning given the extraordinary importance of accurate pre-transfusion testing and the ability to provide blood components to patients in a timely, often emergent, basis.

As opposed to other forms of laboratory testing such as those in clinical chemistry, coagulation, and hematology, blood bank testing has defied the development of rapid, high-throughput automation. The methods for blood bank automation that are currently available require, in essence, the use of a machine that detects the agglutination of red cells, but agglutination (or some variant thereof) is still the end-point much as it was nearly 100 years ago. Reasons for the difficulty in developing truly automated blood typing systems are multiple, but in large part have to do with the need to work with intact cells in order to detect the presence of specific polymorphic molecules on their surfaces. This is in contrast to other laboratory tests that simply count numbers of cells or measure the concentrations of soluble plasma proteins or electrolytes.

While it is true that flow cytometric testing also detects cell-surface phenotype, the indications for such tests do not, in general, require rapid real-time results such as those required in transfusion medicine where the goal is to prevent the transfusion of incompatible blood, often during emergencies such as trauma or unanticipated surgery, where time and accuracy are of the essence. Furthermore, essential differences in the nature of blood bank testing have precluded the development of "point-of-care" testing devices, such as those now available for glucose or electrolyte determinations or for the rapid "on-the-scene" diagnosis of myocardial infarction.

The development of novel blood bank testing methods could lead to the development of small, portable devices for pre-transfusion testing that could facilitate "point-of-care" (e.g., battlefield) testing not possible using conventional approaches.

Another significant issue in blood banking testing is the growing unavailability of complete panels of high-quality immunological reagents for typing. Supplies of conventional sources come from donated human polyclonal antisera that are difficult to quality control and are dwindling in supply due to growing ethical concerns regarding the deliberate hyper-immunization of reagent donors. Because immune responses to many blood group antigens are mounted only in humans (who lack the particular antigen) and not in animals (e.g., mice, whose immune systems generally cannot detect the subtle human polymorphisms to which the antisera needs to be directed), efforts to produce monoclonal typing reagents have required the ability to transform human B-cells, which is a very inefficient and expensive endeavor. Therefore, the availability of endless supplies of well-characterized monoclonal RBC antibodies, analogous to those which revolutionized the automation of other immunological-based assays, such as those for endocrinology or infectious diseases, has been problematic in the field of transfusion medicine.

More than 20 million units of blood are collected in the United States annually, with worldwide collections exceeding 40 million units. Blood collection centers (e.g., American Red Cross, hospital-based donor centers), hospitals, and other blood banks and transfusion centers all have on-going needs to type blood quickly and accurately in a high-throughput manner. Small, automated, blood typing instruments would also have "point-of-care" applications in physician offices such as those of obstetricians in which a patient's Rh type needs to be determined in order to properly administer Rh(D)-immune globulin. Each unit of blood that is collected is typed for at least 3 (i.e., A, B, Rh(D)) antigens and often the blood is tested for detection of many more antigens (e.g., Rh(C), Rh(c), Rh(E), Rh(e), K, $Fy^a$, $Fy^b$, M, N, S, s, $Jk^a$, $Jk^b$, and the like).

Upon receipt of units by a blood bank, standards require that each unit be retested for A and B to ensure proper labeling. Each collected unit of blood is separated into red cells, platelets, and plasma in order to treat 3 different patients with different needs. Approximately twice as many patients are typed for A, B, and Rh(D) (and often other antigens) than those who actually receive blood (i.e., crossmatch/transfusion ratio is approximately 2). In addition, blood samples are collected every seventy-two hours on hospitalized patients in order to have fresh samples available for cross-matching purposes such that many patients are typed and retyped many times during their hospitalization. Therefore, the number of blood typings performed worldwide annually is in the hundreds of millions of tests.

As noted previously, essentially all methods for RBC typing, whether manual or automated, use agglutination as the endpoint. The disadvantages of manual methods include labor costs, low throughput, and human error. Disadvantages of current automated methods include inability to multiplex testing reactions and relatively low throughput when compared to other laboratory testing. Additionally, significant disadvantages of both current manual and automated methods include their reliance on conventional sources of antisera, which sources are dwindling in supply and can potentially transmit human disease, or the few human or mouse hybridoma-produced antibodies which are difficult and expensive to produce. The present invention provides endless supplies of inexpensive phage-displayed anti-RBC reagents that can be used not only in an automated "phenotyping-by-reagent genotyping" technology as disclosed herein, but that are also compatible with conventional manual and automated agglutination methods using anti-M13 antibody as the agglutinating (i.e. "Coombs") agent (e.g., U.S. Pat. No. 5,985,543, to Siegel).

In sum, there is a long-felt and acute need for improved blood typing methods and reagents therefore, which will allow the automation of such tests thereby lowering costs, improving efficiency and accuracy, and obviating the need for current difficult to obtain reagents. The present invention meets these needs.

BRIEF SUMMARY OF THE INVENTION

The invention includes a method of detecting the presence of an antigen-bearing moiety on a cell. The method comprises, a) contacting a cell with a bacteriophage expressing an antibody known to specifically bind with the antigen-bearing moiety wherein the bacteriophage comprises a nucleic acid and wherein the sequence of the nucleic acid is at least partially known; b) denaturing any bacteriophage specifically bound with the cell to release the nucleic acid; and c) detecting the nucleic acid, wherein detecting the nucleic acid detects the presence of the antigen-bearing moiety on the cell, thereby detecting the presence of the antigen-bearing moiety on the cell.

In one aspect, the method further comprises amplifying the nucleic acid prior to step (c).

In another aspect, the method further comprises washing the cell between step (a) and step (b).

In yet another aspect, the cell is a red blood cell and the antigen-bearing moiety is a red blood cell antigen.

In a further aspect, the red blood cell antigen is selected from the group consisting of A, B, Rh(D), Rh(C), Rh(c), Rh(E), Rh(e), K, $Fy^a$, $Fy^b$, M, N, S, s, $Jk^a$, and $Jk^b$.

In one aspect, the cell is a white blood cell and the antigen-bearing moiety is selected from the group consisting of a lymphocyte antigen, a monocyte antigen, and a granulocyte antigen.

In yet another aspect, the cell is a platelet and the antigen-bearing moiety is a platelet antigen.

In a further aspect, the platelet antigen is selected from the group consisting of HPA-1a, HPA-1b, HPA-2a, HPA-2b, HPA-3a, HPA-3b, HPA-4a, HPA-4b, HPA-5a, HPA-5b, HPA-6b, HPA-7b, HPA-8b, HPA-9b, HPA-10b, $Gov^a$, and $Gov^b$.

In another aspect, the nucleic acid comprises a sequence complementary to a molecular beacon probe.

In a further aspect, the sequence is complementary to a sequence selected from the group consisting of the sequence of SEQ ID NO:3 and the sequence of SEQ ID NO:4.

In yet a further aspect, the sequence of the molecular beacon probe is selected from the group consisting of the sequence of SEQ ID NO:7, the sequence of SEQ ID NO:8, the sequence of SEQ ID NO:9, and the sequence of SEQ ID NO:10.

In another aspect, the molecular beacon probe comprises a fluorophore.

In one aspect, the nucleic acid is amplified using polymerase chain reaction (PCR).

In another aspect, the PCR comprises using a primer selected from the group consisting of the sequence of SEQ ID NO:1 and the sequence of SEQ ID NO:2.

In yet another aspect, the nucleic acid is amplified by transcription using immuno-detection amplified by T7 RNA (IDAT).

The invention includes a method of detecting the presence of at least two different antigen-bearing moieties on a cell. The method comprises: a) contacting a cell with a first bacteriophage expressing an antibody known to specifically bind with a first antigen-bearing moiety wherein the first bacteriophage comprises a first nucleic acid and wherein the sequence of the first nucleic acid is at least partially known; b) contacting the cell with a second bacteriophage expressing an antibody known to specifically bind with a second antigen-bearing moiety wherein the second bacteriophage comprises a second nucleic acid and wherein the sequence of second the nucleic acid is at least partially known and wherein the sequence of the first nucleic acid is detectably different from the sequence of the second nucleic acid; c) detecting the binding of the first bacteriophage with the antigen-bearing moiety by detecting the presence of the first nucleic acid, wherein detecting the first nucleic acid detects the presence of the first antigen-bearing moiety on the cell; d) detecting the binding of the second bacteriophage with the antigen-bearing moiety by detecting the presence of the second nucleic acid, wherein detecting the second nucleic acid detects the presence of the second antigen-bearing moiety on the cell; thereby detecting the presence of at least two different antigen-bearing moieties on the cell.

The invention also includes a method of detecting the presence of an anti-red blood cell antibody in human serum. The method comprises: a) contacting a human red blood cell expressing at least one human red blood cell antigen on the surface of the cell with the serum; b) washing the cell to remove any antibody bound non-specifically with the cell; c) contacting the cell with a bacteriophage expressing an anti-humanglobulin reagent wherein the bacteriophage comprises a nucleic acid and wherein the sequence of the nucleic acid is at least partially known; d) denaturing any bacteriophage specifically bound with the cell to release the nucleic acid; and e) detecting the nucleic acid, wherein detecting the nucleic acid detects the presence of the anti-red blood cell antibody in the serum.

In one aspect, the anti-humanglobulin reagent is selected from the group consisting of an anti-human IgG, an anti-human IgM, an anti-human kappa/lambda light chain antibody, a staphylococcal Protein A, a streptococcal Protein G, and a peptostreptococcal Protein L.

In another aspect, the method further comprises amplifying the nucleic acid before step (e).

In yet another aspect, the antibody is selected from the group consisting of an autoantibody and an alloantibody.

The invention includes a method of detecting the presence of anti-red blood cell autoantibody in a human. The method comprises: a) obtaining a red blood cell from the human; b) washing the cell to remove any antibody bound non-specifically with the cell; c) contacting the cell with a bacteriophage expressing an anti-humanglobulin reagent wherein the bacteriophage comprises a nucleic acid and wherein the sequence of the nucleic acid is at least partially known; d) denaturing any bacteriophage specifically bound with the cell to release the nucleic acid; and e) detecting the nucleic acid, wherein detecting the nucleic acid detects the presence of the anti-red blood cell autoantibody in the human.

In one aspect, the method further comprises amplifying the nucleic acid before step (e).

The invention includes a method of detecting the presence of a ligand in a sample. The method comprises: a) contacting a cell with a bacteriophage expressing a receptor known to specifically bind with the ligand wherein the bacteriophage comprises a nucleic acid and wherein the sequence of the nucleic acid is at least partially known; b) denaturing any bacteriophage specifically bound with the cell to release the nucleic acid; and c) detecting the nucleic acid, wherein detecting the nucleic acid detects the presence of the ligand in the sample.

In one aspect, the ligand is present on a cell.

In another aspect, the sample is a biological sample obtained from a human.

In yet another aspect, the biological sample is a cell sample.

In a further aspect, the cell sample comprises a red blood cell and the ligand is a red blood cell antigen and further the receptor is an antibody.

In another aspect, the method further comprises amplifying the nucleic acid prior to detection in step (c).

The invention includes a kit for detecting the presence of an antigen-bearing moiety on a cell. The kit comprises a bacteriophage expressing an antibody known to specifically bind with the antigen-bearing moiety wherein the bacteriophage comprises a nucleic acid and wherein the sequence of the nucleic acid is at least partially known. The kit further comprises an applicator, and an instructional material for the use of the kit.

In one aspect, the antigen-bearing moiety is a red blood cell antigen selected from the group consisting of A, B, Rh(D), Rh(C), Rh(c), Rh(E), Rh(e), K, Fy$^a$, Fy$^b$, M, N, S, s, Jk$^a$, and J$^b$.

In another aspect, the kit further comprises a molecular beacon probe wherein the nucleic acid sequence of the probe is selected from a sequence complementary to a sequence selected from the group consisting of the sequence of SEQ ID NO:3 and the sequence of SEQ ID NO:4.

In yet another aspect, the sequence of the molecular beacon probe is selected from the group consisting of the sequence of SEQ ID NO:7, the sequence of SEQ ID NO:8, the sequence of SEQ ID NO:9, and the sequence of SEQ ID NO:10.

In a further aspect, the kit further comprises a PCR primer.

In yet a further aspect, the sequence of the primer is selected from the group consisting of the sequence of SEQ ID NO:1 and the sequence of SEQ ID NO:2.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 4, comprising

DETAILED DESCRIPTION OF THE INVENTION

Definitions

Figure 1:
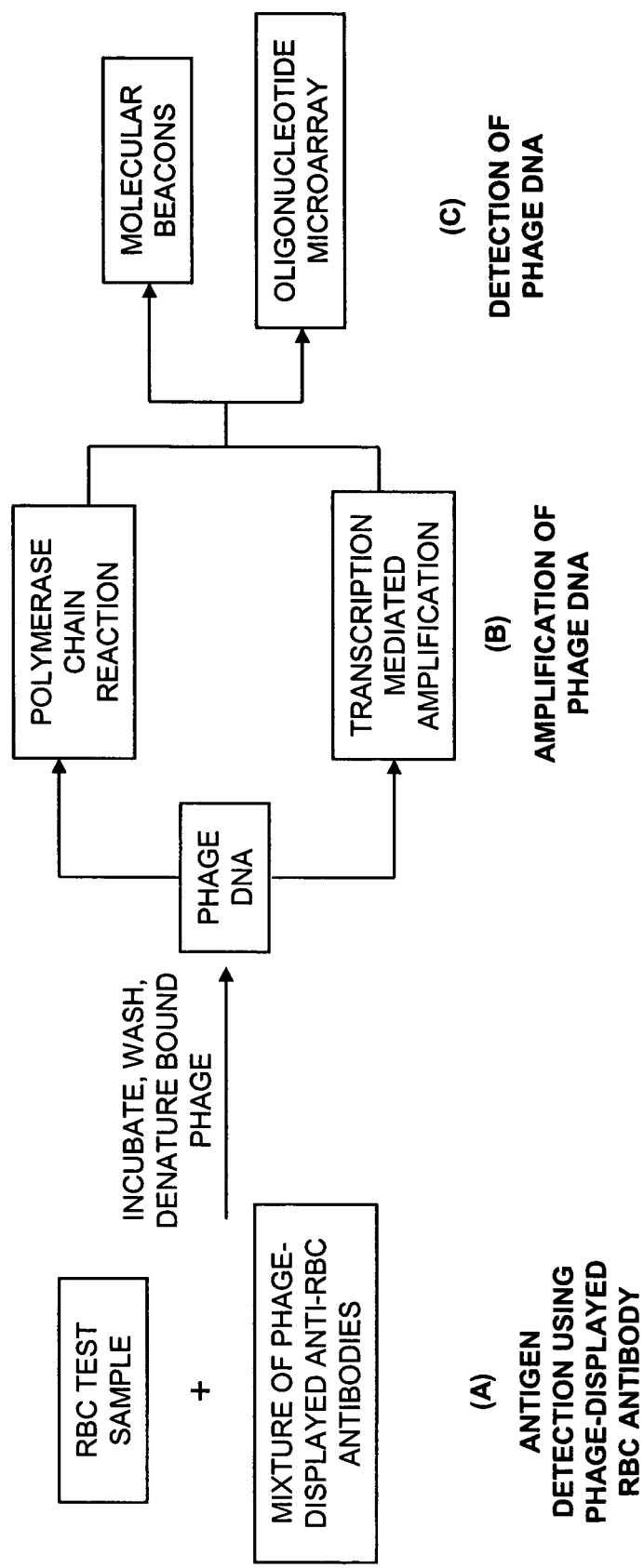
FIG. 1 is a diagrammatical outline of technical plan illustrating use of (A) phage-displayed anti-RBC antibodies, (B) phage DNA amplification, and (C) phage DNA detection without replica plating.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By the term "antigen-bearing moiety" as used herein, is meant a molecule to which an antibody binds. The antigen-bearing moiety may be a membrane bound protein which is selected from the group consisting of an antigen and a receptor. In another aspect, the membrane bound protein is an antigen, such as a red blood cell antigen, such as Rh antigen. When the antigen-bearing moiety is a carbohydrate, it may be a carbohydrate expressed on a glycolipid, for example, a P blood group antigen or other antigen.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease means reducing the severity of one or more symptoms of the disease.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The terms "bacteriophage" and "phage" are used interchangeably herein and refer to viruses which infect bacteria. By the use of the terms "bacteriophage library" or "phage library" as used herein, is meant a population of bacterial viruses comprising heterologous DNA, i.e., DNA which is not naturally encoded by the bacterial virus.

By the term "applicator," as the term is used herein, is meant any device including, but not limited to, a hypodermic syringe, a pipette, and the like, for administering the bacteriophage expressing a receptor (e.g., an antiglobulin reagent, an antibody, an anti-antibody, and the like), a cell, a sample, primers, molecular beacon probe, dNTPs, T7 RNA polymerase, and the like, of the invention to a cell, a sample, and the like.

"Biological sample," or simply "sample", as that term is used herein, means a sample, such as one that is, but need not be, obtained from an animal, which sample is to be assessed for the presence of a biological organism, or component thereof, such that the sample can be used to assess the presence, absence and/or level, of an antigen, or ligand, of interest according to the methods of the invention. Such sample includes, but is not limited to, any biological fluid (e.g., blood, lymph, semen, sputum, saliva, phlegm, tears, and the like), fecal matter, a hair sample, a nail sample, a brain sample, a kidney sample, an intestinal tissue sample, a tongue tissue sample, a heart tissue sample, a mammary gland tissue sample, a lung tissue sample, an adipose tissue sample, a muscle tissue sample, and any sample obtained from an animal that can be assayed for the presence or absence of an antigen. Further, the sample can comprise an aqueous sample (e.g., a water sample) however obtained, to be assessed for the presence of an organism, or a component thereof, such as a drinking water sample, before or after any treatment, wherein the presence of a biological organism (e.g., a Cryptosporidium organism) is assessed.

As used herein, the term "fragment" as applied to a nucleic acid, may ordinarily be at least about 20 nucleotides in length, preferably, at least about 30 nucleotides, more typically, from about 40 to about 50 nucleotides, preferably, at least about 50 to about 80 nucleotides, even more preferably, at least about 80 nucleotides to about 90 nucleotides, yet even more preferably, at least about 90 to about 100, even more preferably, at least about 100 nucleotides to about 150 nucleotides, yet even more preferably, at least about 150 to about 200, even more preferably, at least about 200 nucleotides to about 250 nucleotides, yet even more preferably, at least about 250 to about 300, more preferably, from about 300 to about 350 nucleotides, preferably, at least about 350 to about 360 nucleotides, and most preferably, the nucleic acid fragment will be greater than about 365 nucleotides in length.

As used herein, the term "fragment" as applied to a polypeptide, may ordinarily be at least about 20 amino acids in length, preferably, at least about 30 amino acids, more typically, from about 40 to about 50 amino acids, preferably, at least about 50 to about 80 amino acids, even more preferably, at least about 80 amino acids to about 90 amino acids, yet even more preferably, at least about 90 to about 100, even more preferably, at least about 100 amino acids to about 120 amino acids, and most preferably, the amino acid fragment will be greater than about 123 amino acids in length.

By the term "Fab/phage" as used herein, is meant a phage particle which expresses the Fab portion of an antibody.

By the term "scFv/phage" are used herein, is meant a phage particle which expresses the Fv portion of an antibody as a single chain.

"Phage," or "phage particle," as these terms are used herein, include that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make "phage-like" particles. That is, these particles resemble phage on the outside, but on the inside they contain plasmid (also referred to as a "phagemid") DNA. In other words, the phagemid DNA need not encode any M13 phage proteins, except a piece of M13 gene III fused to the DNA for antibody or peptide. Thus, it should be understood that the terms "phage," "phage particle," "phage-like particle" and "phagemid" are used interchangeably herein.

A "disease" is a state of health of an animal wherein the animal cannot maintain homeostasis, and wherein if the disease is not ameliorated, then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGGC3' share 50% homology.

"Instructional material," as that term is used herein, includes a publication, a recording, a diagram, or any other medium of expression which can be used to communicate the usefulness of the nucleic acid, peptide, and/or compound of the invention in the kit for detecting the presence of an antigen-bearing moiety on a cell of interest, and/or for detecting an autoantibody in serum. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids that have been substantially purified from other components that naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene that is expressed in a recombinant host cell wherein the gene comprises a recombinant polynucleotide, produces a "recombinant polypeptide."

A "recombinant polypeptide" is one that is produced upon expression of a recombinant polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding a chromogenic substrate, e.g., o-nitrophenyl-β-D-galactopyranoside, to the medium (Gerhardt et al., eds., 1994, Methods for General and Molecular Bacteriology, American Society for Microbiology, Washington, D.C., p. 574).

A "receptor" is a compound that specifically binds with a ligand. This term includes a protein, such as an antibody, an antiglobulin reagent, and the like, that when expressed by a phage and contacted with its cognate ligand, binds specifically therewith.

The term "ligand," as used herein, refers to any protein or proteins that can interact with a receptor binding domain, thus having a "binding affinity" for such domain. Ligands can be soluble or membrane bound, and they can be a naturally occurring protein, or synthetically or recombinantly produced. The "ligand" can also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule that interacts directly or indirectly with the ligand.

By the term "specifically binds," as used herein, is meant a molecule, e.g., a protein, a nucleic acid, an antibody, a compound, and the like, which recognizes and binds a specific molecule, but does not substantially recognize or bind other molecules in a sample. For instance, an antibody which recognizes and binds a cognate ligand (i.e., an antigen-bearing moiety present on a cell) in a sample, but does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.
Description The invention relates to methods for detecting the presence of a molecule of interest on a cell or in a biological sample. Typically, a red blood antigen expressed on a RBC surface is detected, but the invention encompasses detecting the presence of numerous antigens of interest on a wide plethora of cells, including, but not limited to, red and white blood cells, as well as platelets, and cells used for transplantation therapy, and the identification of antigens on cells for forensic purposes (e.g., hair, skin, nail, sperm, saliva, and other cells), among many other uses.

The invention also relates to detection of an antigen of interest in a biological sample. Such a sample includes an aqueous sample to detect the presence of any organism, or component thereof, in the sample.

The invention relates to using an antibody, specific for a known antigen, displayed by a phage (e.g., an M13, T7, lambda, eukaryotic, and the like), to detect the presence of the antigen on a cell or in a biological sample. More specifically, phage specifically bound with a cell are detected by assaying for the nucleic acid contained in the phage particle. That is, the nucleic acid sequence of the nucleic acid contained in the phagemid is at least partially known, such that techniques for detecting nucleic acids can be used to assess the presence of the sequence, thereby detecting, in a novel process referred to herein as "phenotyping-by-reagent-genotyping", the antigen.

Essentially, the bacteriophage nucleic acid acts like a tag for detecting an antigen recognized by the antibody encoded by the phage. In this way, the high sensitivity and high throughput screening properties of nucleic acid detection methods can be applied to the immunological detection of an antigen, thereby combining the advantages of both technologies. The crucial features of this approach are that the specificity of the antibody displayed by the bacteriophage and the nucleic acid sequence, or a portion thereof, of the DNA contained within the phage, both be known. It would be understood, based upon the disclosure provided herein, that the precise nature of the antigen, be it a protein, carbohydrate, lipid, or any other compound, recognized by the antibody, need not be known, only that the specificity of the antibody for that antigen be known. For instance, where an antibody is known to bind with and identify a cancer cell (or any cell associated with a disease), but not bind with an otherwise identical cell that is not cancerous (or associated with a disease), the antibody can be used to detect a cancer (or disease state) using the methods of the invention. That is, the antibody binding with a test cell or a biological sample, can be detected by detecting the nucleic acid present in the phage particle encoding the antibody portion, thereby detecting a cancer cell, without having to know the precise nature of the antigen present on the cancer (or disease-associated) cell.

The invention further relates to detection of multiple antigens of interest on a cell in a single tube assay. That is, bacteriophage that encode antibodies specific for at least two different antigens can be used to detect those antigens on a cell. More specifically, each phage encodes an antibody that specifically binds with a known antigen and each phage encodes an antibody that recognizes a different antigen, or antigen-moiety. Further, each phage contains a DNA molecule comprising a sequence that is known, wherein the sequence differs between the phage. Using this approach, the presence of a plurality of antigens of interest can be readily assessed by simply using a panel of phage, each displaying an antibody specific for one of the antigens, where the nucleic acid molecule of each phage comprises a known sequence that is distinguishable from that of any other phage in the panel. In this way, multiple antigens can be assayed for using a single reaction step. This "multiplexing" method is not possible using conventional methods that identify the binding of antigen-specific antibodies to a cell since the secondary anti-antibody antibody used to detect the antigen-specific antibodies typically cross-reacts with all the antigen-binding antibodies, or it cannot be determined which antigen-specific antibody the second antibody is bound with. In the case of conventional methods for phenotyping red blood cells, in which antibodies directly agglutinate the appropriate cell type (i.e., no secondary antibody needed), if mixed together, it would likewise not be possible to determine which antigen-specific antibody was responsible for the agglutination. This multiplex approach allows the rapid simultaneous detection of a plurality of antigens using only a single sample.

Further, the invention relates to identification of anti-red blood cell antibodies in serum. That is, a panel of RBCs, expressing various known antigens on their surfaces, can be contacted with a serum sample. Reagent RBCs, expressing characterized antigens, are commercially available (e.g., Johnson & Johnson, Raritan, N.J.). The cells are then washed to remove any antibodies non-specifically adhering to the cells and the cells are then contacted with bacteriophage displaying an anti-globulin reagent.

Additionally, autoantibodies present in a patient can be detected by obtaining RBCs from the patient, washing them to remove any antibodies and/or complement that is non-specifically bound with the cells, and the cells can then be contacted with a phage expressing an antihumanglobulin reagent. Thus, by detecting a nucleic acid sequence contained by the phage, the presence of autoantibody on the patient cells, as well as the presence of complement deposited on the cells due to the autoantibody, can be readily detected according to the novel "phenotyping-by-reagent-genotyping" methods disclosed herein.

Conventionally, screening and identification of serum antibodies using reagent red cells displaying known antigens is referred to in the art as an "antiglobulin test", one such test is a Coombs reaction. These assays detect the presence of an antibody, or complement deposited thereby, on a cell of interest. Because complement, while not an antibody, is considered a "globulin", the reagents used to detect antibodies and/or complement are referred to in the art as "antiglobulin" reagents.

These assays, which detect antibodies and/or complement fragments (e.g., C3d) on patient red cells to detect anti-red cell autoantibodies, or the complement they deposit, and also to detect patient alloantibodies, or the complement they deposit, can be used to identify autoantibodies, alloantibodies, or both, that could be destroying autologous cells or transfused cells in a hemolytic transfusion reaction.

As used herein, an "antiglobulin reagent" is a reagent that can detect antibodies, complement, or both. Thus, the present invention includes, as would be understood by one skilled in the art armed with the teachings provided herein, antiglobulin reagents comprising, among others, e.g., anti-antibody antibodies, anti-complement antibodies, Protein A, Protein G, or Protein L, that is, the invention encompasses expression by phage of a wide plethora of reagents that would be understood by the skilled artisan to specifically bind with a globulin, such as antibody, complement, and the like. That is, the present invention includes using an antiglobulin reagent expressed by a phage including, but not limited to, an "anti-antibody antibody", an anti-complement, and any reagent known to bind a globulin (e.g., an antibody, complement, and the like). Additionally, phage expressing Protein A, or an immunoglobulin-binding domain thereof, have been described previously (e.g., Djojonegoro et al., 1994, Bio/Technol. 12:169-172). Such antiglobulin reagent-expressing phage can be used in the methods disclosed herein as would be understood by one skilled in the art armed with the teachings provided herein.

The invention relates to identifying autoantibodies in a serum sample obtained from a patient, or autoantibodies or complement fragments pre-deposited on patient cells in vivo, both characteristics of a disease such as, but not limited to, autoimmune hemolytic anemia. That is, serum obtained from the patient is contacted with an aliquot of reagent RBCs, such as those that are commercially available. RBC autoantibodies bind to common antigens present on essentially all red cells, not just of the patient. Thus, the patient cannot be transfused with blood from another human since the autoantibodies present in the patient serum with also react with the donor RBCs. Because the patient's RBCs are already be coated with the autoantibodies, those autoantibodies already on the cells from having been bound in vivo can be detected according to the methods of the invention by assaying the cells directly using antihumanglobulin reagent expressed on a phage. Alternatively, detecting autoantibodies is performed the same way as is detection of alloantibodies—by contacting the patient serum with reagent red cells. In the case of alloantibodies, only certain reagent RBCs will bind the antibodies, and knowing the precise phenotype of those cells identifies the antigen specificity. In the case of autoantibodies, typically all reagent red cells will bind the antibodies because the autoantigens are present on all cells. Any antibody specifically bound with the RBCs is then detected according to the methods of the invention such as, as more fully disclosed elsewhere herein, by contacting the cells with a phage expressing an antiglobulin reagent and detecting the binding of the phage with the cells by detecting a nucleic acid contained by the phage, i.e., by performing "phenotyping-by-reagent-genotyping" according to the methods of the invention. In this way, autoantibodies present in human serum can be readily detected using the methods disclosed herein analogous to the conventional "indirect antiglobulin test". Furthermore, by contacting patient RBCs with antiglobulin-expressing phage particles and detecting the binding of the phage with the cells by detecting a nucleic acid contained by the phage, one can detect the presence of in vivo-deposited autologous antibodies and/or complement fragments on patient RBCs. This assay is analogous to the conventional "direct antiglobulin test".

Further, the invention relates to performing compatibility testing between patient serum and red cells drawn from prospective units of blood to be transfused to the patient (i.e., patient/donor "crossmatching"). That is, an aliquot of RBCs from a prospective unit of donor blood can be contacted with a serum sample from a potential transfusion recipient. The cells are then washed to remove any antibodies non-specifically adhering to the cells and the cells are then contacted with bacteriophage displaying an antiglobulin reagent. Thus, the present invention provides methods for detecting an alloantibody in a patient that is to be transfused thereby allowing proper patient/donor crossmatching to prevent incompatible transfusion.

I. Methods

A. Methods of Detecting an Antigen

The invention includes a method for detecting the presence of an antigen-bearing moiety on a cell. The method comprises contacting a cell with a bacteriophage expressing an antibody that is known to specifically bind with the antigen-bearing moiety when it is present on a cell. Such phage-displayed antibodies, as well as methods for their production, are well-known in the art, and are described in, among others, U.S. Pat. No. 5,876,925, No. 5,985,543, and No. 6,255,455, all to Siegel. These antibody-displaying bacteriophage are exemplified herein by phage displaying anti-Rh(D) and anti-B specific antibodies. However, the skilled artisan would understand, based upon the disclosure provided herein, that the invention is not limited to these, or any other, particular antibodies displayed on the specific bacteriophage disclosed herein. Rather, the antibody displayed by the phage can be specific for any cell component and techniques for producing phage-displaying antibodies to antigens of interest are well-known in the art, and are encompassed in the present invention.

The procedures for making a bacteriophage library comprising heterologous DNA are well known in the art and are described herein in, as well as in for example, in Sambrook et al., supra. Bacteriophage which encode a desired antibody can be engineered such that the antibody protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Methods relating to production of such display libraries, and the screening thereof, are set forth in U.S. Pat. No. 6,255,455, to Siegel, which is incorporated by reference as if set forth in its entirety herein. Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors (or phagemids with M13 packaging signals) creating a library of phage which express human Fab (or scFv) fragments on their surface. Phage which display the antibody of interest are selected by antigen binding and are propagated in bacteria to produce soluble human Fab (or scFv) immunoglobulin. Thus, in contrast to conventional monoclonal antibody synthesis, this procedure immortalizes DNA encoding human immunoglobulin rather than cells which express human immunoglobulin.

Although the bacteriophage displaying antibodies of interest herein are exemplified by M13 phage, the present invention is not limited to these, or any other, vector displaying an antibody. Instead, one skilled in the art would appreciate, armed with the teachings provided herein, that any vector that can display an antibody, wherein the vector comprises a nucleic acid the sequence of which is at least partially known, can be used in the methods disclosed herein. Therefore, while the antibody-displaying bacteriophage disclosed herein are exemplified by M13, other bacteriophage, such as lambda phage or T7 phage, can also be useful in the method of the invention. Lambda phage display libraries have been generated which display peptides encoded by heterologous DNA on their surface (Sternberg et al., 1995, Proc. Natl. Acad. Sci. USA 92:1609-1613) as have T7 phage display libraries (Hansen et al., 2001, Int. J. Oncol. 19:1303-1309).

Moreover, it is contemplated that the method of the invention may be extended to include viruses other than bacteriophage, such as eukaryotic viruses. In fact, eukaryotic viruses can be generated which encode genes suitable for delivery to a mammal and which encode and display an antibody capable of targeting a specific cell type or tissue into which the gene is to be delivered. For example, retroviral vectors have been generated which display functional antibody fragments (Russell et al., 1993, Nucl. Acids Res. 21:1081-1085). These, and any other vector expressing an antibody can be used in the methods of the invention and are encompassed thereby.

Furthermore, while the method of the invention as exemplified herein describes using phage which encode the Fab portion or an scFv portion of an antibody molecule, the method should not be construed to be limited solely to the use of phage encoding Fab or scFv antibodies. Fab molecules comprise the entire Ig light chain, that is, they comprise both the variable and constant region of the light chain, but include only the variable region and first constant region domain (CHI) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted as described herein for phage libraries comprising Fab DNA.

The invention should also be construed to include synthetic phage display libraries in which the heavy and light chain variable regions may be synthesized such that they include nearly all possible specificities. Therefore, antibody-displaying libraries can be "natural" or "synthetic" (Barbas, 1995, Nature Medicine 1:837-839; de Kruif et al., 1995, J. Mol. Biol. 248:97-105). Antibody-displaying libraries comprising "natural" antibodies are generated as described in, e.g., U.S. Pat. No. 5,876,925, to Siegel. Antibody-displaying libraries comprising "synthetic" antibodies are generated following the procedure described in Barbas (1995, supra) and the references cited therein.

The skilled artisan would appreciate, based upon the disclosure provided herein, that the red blood cell antibodies to which antibodies can be generated using methods known in the art and can then be used in the method of the invention include, but are not limited to, Rh antigens, including Rh(D), Rh(C), Rh(c), Rh(E), Rh(e), and other non-Rh antigens, including red blood cell antigens in the Kell, Duffy, Lutheran and Kidd blood groups.

Thus, the method of the invention can be used for detection of any RBC antigen or other cell antigen, such as, but not limited to, tumor-specific antigen, bacterial antigens, and the like. The method of the invention is also useful for typing platelets by generating phage antibodies specific for a number of clinically important platelet antigens, notably, HPA-1a/1b, HPA-2a/2b, HPA-3a/3b, and the like.

The invention is further useful for typing donor white blood cells for HLA antigens for the purposes of matching donors and recipients for potential transplant matching in the case of both solid (for example, kidney, heart, liver, lung) and non-solid (for example, bone marrow) organ or tissue transplanting.

In addition, the methods of the present invention can be used for forensic purposes, to detect any antigen of interest in a sample, where the sample can be, but is not limited to, bone, hair, skin, semen, saliva, or any other sample that can be obtained from an organism or biological sample. The only feature required is that the sample contain an antigen that can be specifically recognized by an antibody expressed by a bacteriophage, or other antibody-displaying vector. Thus, the present invention is not limited in any way to the detection of any particular antigen; instead, the invention encompasses detecting a wide plethora of antigens of interest using the novel "phenotyping-by-reagent-genotyping" detection methods disclosed herein.

Thus, the invention encompasses detecting an antigen of interest on a red blood cell, referred to herein as "phenotyping," by detecting the binding of a phage expressing an anti-red blood cell antibody, where the phage is detected by detecting a known sequence present in the nucleic acid contained by the phage particle, which is referred to herein as "phenotyping-by-reagent-genotyping." Further, the invention includes screening of patient sera for anti-red blood cell antibodies using phage particles that display anti-human IgG (or anti-IgM or anti-kappa/lambda light chain antibody which would pick up any Ig isotype). Again, the phage bound with the RBCs is detected by detecting a nucleic acid sequence present in the nucleic acid contained by the phage.

Additionally, the invention encompasses using the phenotyping-by-reagent-genotyping method in an immune assay, whether the antigen being detected is on a cell or not (e.g., antigens such as, but not limited to, any measured for research or clinical purposes from a cytokine to HCG for a pregnancy test). That is, the present invention combines the specificity conferred by immunoglobulins for a given substance, which specificity takes into account any post-translational modification (e.g., phosphorylation, glycosylation, and the like), with the sensitivity conferred by nucleic acid detection methods—as well as the ability to perform multiplex assays. That is, a sample being assayed would be applied such that its components are affixed to a solid support, such as coating the well of a plate for an ELISA, nitrocellulose filter, bead, or any other solid support, and the phage expressing a protein that specifically binds with a cognate ligand can be allowed to bind with the components affixed to the solid support. Any phage specifically bound to a cognate ligand can be detected by detecting a known nucleic acid sequence specified by the nucleic acid contained within the phage. Thus, the presence of any ligand of interest can be detected using the "phenotyping-by-reagent-genotyping" method disclosed herein even where the sample being assayed does not comprise a cell.

Moreover, the skilled artisan would appreciate, based upon the disclosure provided herein, that the invention encompasses the phenotyping of other blood cells (e.g., platelets, white cells, and the like) and the detection of antibodies to those cells in the blood (e.g., anti-platelet auto- or alloantibodies, anti-HLA antibodies, etc.), such that the present invention is not limited to red blood cells. Indeed, the invention is not limited to blood cells at all, but can be used to detect any molecule of interest present on any kind of cell. Thus, one skilled in the art would appreciate, based upon the disclosure provided herein, that the present invention includes, but is not limited to, detecting a molecule of interest on a cell where flow cytometry would otherwise be used such that the wide plethora of antibodies now available (e.g., hundreds of anti-CD antibodies, such as anti-CD4 or CD-8 for helper/suppressor T cells, anti-CD20 for B cells, and the like) can be expressed on a phage and used to detect, according to the novel methods disclosed elsewhere herein, whether the antigen is present in a cell. The present invention includes using antibodies to be developed in the future to antigens of interest as these are developed and used according to the methods disclosed herein.

The skilled artisan would appreciate, based upon the teachings provided herein, that detection of any molecule of interest, for instance, with regard to forensic application of the methods disclosed herein, provides an important advantage over present methods in that many antigens important for identifying the origin of fluids (blood or soluble substances in saliva, and the like) are carbohydrates (like the A and B antigens). Using genetic testing on the miniscule spot for DNA cannot amplify the DNA that encodes carbohydrates because DNA does not encode carbohydrates which are products of post-translational modification of proteins. Prior art methods relating to carbohydrate detection are limited to detecting the DNA for the enzymes (e.g., the glycosytransferases) that are responsible for assembling the sugar moieties onto the protein or lipid. The problem with conventional detection assays is that the ultimate expression of a particular sugar is the result of the inheritance of a number of enzymes that act in precise sequence to assemble the chains such that the genes for all of the enzymes would need to be detected in order to identify the identity of the person the sample was derived from. For example, in order for an individual to be blood group A, the enzyme that adds N-acetylgalactosamine onto its precursor sugar is required, as is the enzyme (a fucosyl transferase) to assemble the precursor sugar. Other carbohydrates (like P) are even more complicated in their structures and assembly. If the sample comprises a mixture of secretions in one spot from different individuals, DNA testing would pick up all enzymes and the test would not be able to distinguish whether one person had all the enzymes and could make a particular sugar antigen or if the sample comprised DNA from various persons who could each only produce the various sugar components. Unlike conventional nucleic acid-based testing, the present invention provides the advantage of combining the exquisite specificity of an antibody that is capable of recognizing a complex structure, such as a glycan, and the ability to detect miniscule quantities of a nucleic acid; thus, detection of the nucleic acid contained by the phage, combined with the specificity of an antibody, provide a novel assay with the extraordinary sensitivity and specificity required in forensic uses.

One skilled in the art, based upon the disclosure provided herein, would understand that while the term "phenotyping" is generally used in the art to detecting a characteristic demonstrated by a cell, or organism, the term as used herein with regard to "phenotyping-by-reagent—genotyping", relates to the identification of any antigen of interest, whether or not the antigen is associated with a cell, by detecting a nucleic acid sequence without replica plating. Thus, for instance, the identification of a drug in a dried spot on a car door using a phage-displayed anti-drug antibody according to the methods of the invention, would be "phenotyping" as the term is used herein. Therefore, the methods of the invention, where an antibody expressed by a phage binds with a cognate antigen and the antigen is detected by assaying for a nucleic acid sequence present in the phage DNA, is "phenotyping" as used herein.

Indeed, the skilled artisan, armed with the teachings provided herein, would realize that the present invention is not limited to detection of an "antigen" using phage-displayed antibody (which antibody is then detected by detecting a nucleic acid sequence encoded by the phage DNA). Instead, the present invention encompasses using a non-antibody protein expressed by a phage, which protein specifically binds with a cognate ligand present on a cell, in a sample, or both. Many such binding pairs are well-known in the art and have been identified using a wide variety of assays, including yeast two- and three-hybrid binding assays, among a wide plethora of other assays. Thus, where a binding pair is known in the art, one of the two molecules can be expressed by the phage (the binding pair protein expressed by the phage is referred to herein as the "receptor") and the presence of the other member of the binding pair (referred to as the "ligand" or "target") can be detected by detecting a nucleic acid sequence contained by the phage expressing the receptor protein. The ligand that is to be detected by its cognate receptor/binding partner expressed by the phage can include, but is not limited to, a hormone, or a portion of a hormone where the portion can bind with the receptor displayed by the phage. Further, the methods of the present invention can be used to, inter alia, measure the expression of a hormone receptor on a cell by assessing the amount of a phage displaying the hormone, or portion thereof, which binds with the cell being assayed. The phage specifically bound with the cell due to the receptor/ligand (hormone receptor/hormone expressed by the phage, respectively) interaction can be detected by detecting a nucleic acid sequence present in the nucleic acid contained by the phage as more fully disclosed elsewhere herein.

One skilled in the art would understand, based upon the disclosure provided herein, that the present invention encompasses detection of a molecule of interest that is not associated with a cell. That is, the present invention includes assaying for the presence of a molecule of interest in any sample where the sample can be applied to a solid support such that the molecule of interest can be immobilized. A phage expressing an receptor known to bind specifically with that molecule (herein referred to as a "ligand" or "target" molecule) can then be contacted with the immobilized sample and the binding of any phage can be detected by assaying for the presence of a nucleic acid sequence contained by the phage as more fully described elsewhere wherein. In this way, the present invention can be used to detect a molecule of interest (ligand) present in any sample using the "phenotyping-by-reagent-genotyping" methods disclosed herein.

The skilled artisan would also appreciate, based upon the disclosure provided herein, that a phage can readily expresses a peptide that is known to detect cancer cells but where it is not known what component on the cancer cell the peptide binds with. Thus, the protein known to bind cancer cells can be used to detect a cancer cell even though the identity of the ligand/binding partner that binds with the protein is not known, by detecting bound phage by detecting a nucleic acid sequence contained by the phage, all as more fully disclosed elsewhere herein.

Additionally, where the phage is used to detect the binding of serum antibodies to a reagent red blood cell, the phage can express Staph Protein A, or a portion thereof, instead of anti-IgG, to detect immunoglobulins bound with the RBCs. Therefore, the skilled artisan would appreciate, based upon the disclosure provided herein, that a wide plethora of molecules can be expressed by the phage to detect a cognate binding partner present on a cell, in a tissue or aqueous sample, and the like, and the present invention is not in any way limited to phage expressing an antibody, or to detection of an antigen on a cell, as exemplified elsewhere herein. That is, once a binding pair is known, the skilled artisan, armed with the disclosure provided herein, would readily be able to detect one of the binding pair using the methods of the invention, i.e., by expressing one member of the binding pair on a phage and contacting the phage with a sample, then detecting any phage specifically bound with the sample by detecting a nucleic acid sequence encoded by the phage nucleic acid. This allows the rapid and sensitive detection of a molecule of interest, or various molecules of interest where multiplexing is used, where the molecule is not a nucleic acid, by detecting a nucleic acid.

The specific conditions under which the antibody, or receptor, displayed by the bacteriophage is allowed to specifically bind with an antigen, or ligand, of interest will depend on the specific antigen-antibody and/or receptor-ligand complex involved in the reaction. The skilled artisan would understand, based upon the disclosure provided herein, that such conditions can be readily determined for each antigen/binding pair being detected and the antibody/receptor being used to do so, as is exemplified herein for detection of Rh(D) and B antigens on intact red blood cells using phage expressing antibodies specific for these antigens. These techniques for determining binding conditions are routinely practiced in the art, and are therefore not described further herein.

Once the bacteriophage expressing the antibody (or receptor) are specifically bound with the cell, or ligand in a sample, via the interaction between the antigen-bearing moiety on a molecule of interest present on the cell (ligand) and the antibody expressed by the phage (receptor), the presence of bound phage is detected by detecting the nucleic acid contained in the bacteriophage particle. For the M13 phage exemplified herein, the nucleic acid is a single-stranded DNA molecule, but the present invention is not limited to any particular nucleic acid; rather, any nucleic acid can be detected using techniques well-known in the art (e.g., as described in Sambrook et al., 1989, Molecular Cloning: A Laboratory Manual, Cold Spring Harbor Laboratory, New York; and Ausubel et al., 1997, Current Protocols in Molecular Biology, John Wiley & Sons, New York), some of which are disclosed herein, as well as techniques to be developed in the future, and these various techniques are all encompassed in the invention.

The present invention also encompasses amplification of the nucleic acid to assist in its detection. However, the present invention is not limited to methods requiring the amplification of the nucleic acid. Instead, the skilled artisan, based upon the disclosure provided herein, would appreciate that detection methods which do not require amplification of the nucleic acid are encompassed in the invention. Such detection methods include, but are not limited to, detection of a nucleic acid directly transferred to a chip wherein a fluorescent (or enzyme)-labeled oligonucleotide complementary to the phage(mid) sequence can detect the unamplified nucleic acid. Thus, while FIG. 1 is illustrative of the various techniques that can be used to detect the nucleic acid sequence of interest, the invention is not limited to procedures that require amplification prior to detection of the sequence. Therefore, PCR, IDAT, or other amplification reactions are preferred, but not required, to practice the invention.

The skilled artisan would understand, once armed with the teachings provided herein, that, as exemplified herein, the nucleic acid can be amplified using convention polymerase chain reaction assays. That is, a set of primer sequences can be developed based on the known sequence of the nucleic acid contained by the bacteriophage. As discussed elsewhere herein, the primers can be specific for any portion of the nucleic acid, either the unique sequence comprised in the portion of the nucleic acid encoding the CDR3 portion of the antibody, or any other sequence present in the nucleic acid. Thus, one primer can be complementary to a generic sequence contained in the phage DNA (irrespective of antibody specificity) and the other primer can be complementary to, e.g., a sequence specific to that phage, such as, but not limited to, the CDR3 hypervariable region of the antibody's heavy chain (i.e., the sequence that is unique for a given antibody).

Detection of the amplified nucleic acid indicates the presence of the antigen recognized by the specific antibody encoded by the bacteriophage. The production of PCR primers, and probes that hybridize with the sequence amplified by the PCR, are well-known in the art, and these methods are described in, among others, Sambrook et al. (1989, Molecular Cloning: A Laboratory Manual, Cold Spring Harbor Laboratory, New York), and Ausubel et al. (1997, Current Protocols in Molecular Biology, John Wiley & Sons, New York).

Additionally, the skilled artisan would appreciate, based upon the disclosure provided herein, that sequences can be inserted into the nucleic acid encoding the antibody expressed by the bacteriophage, which inserted sequence can then be detected using various assays known in the art. For instance, as discussed elsewhere herein, "molecular beacons", or as used herein, "beacons" or "beacon sequences," are stem-and-loop-structured oligonucleotides with a fluorescent label at the 5' end and a universal quencher at the 3' end (see, e.g., Tyagi and Kramer, 1996, Nature Biotech. 14:303-308; Broude, 2002, Trends in Biotechnology 20:249-256). When the stem is closed (in the absence of complementary nucleic acid), the fluorophore and quencher are in close proximity and fluorescent energy is absorbed by the quencher and fluorescence is quenched and not detectable. In the presence of complementary nucleic acid, the loop of the beacon hybridizes and the fluorophore and quencher separate such that quenching does not occur. Photons are then emitted from the fluorophore, unquenched, at the wavelength specific for that fluorophore and fluorescence is then detectable. By combining a number of beacons in one tube, each with a different fluorophore at their 5' ends, multiple DNA (Tyagi et al, 1998, Nature Biotech. 16:49-53) or RNA (de Baar et al., 2001, J. Clin. Microbiol. 39:1895-1902) targets can be simultaneously detected by measuring the spectrum of colors emitted from the reaction vessel.

Molecular beacons of two, or more, different colors can be incorporated into a PCR and/or a transcription reaction (e.g., IDAT) to detect the presence of antibody-specific DNA. As described elsewhere herein, the nucleic acid of each bacteriophage, encoding an antibody specific for an antigen of interest, can be modified to insert a unique beacon sequence and each molecular beacon probe can be conjugated to a unique quencher/fluorophore pair such that each beacon, when bound with its complementary sequence, will fluoresce at a unique frequency. In this way, each beacon can be used to detect an antibody binding with an antigen such that the "multiplex" reaction can yield results demonstrating which antigens are present on a cell being examined by assessing which fluorophores are present in the sample. The design and production of such "beacon" sequences, and nucleic acid sequences comprising sequences complementary thereto, are well known in the art.

Armed with the disclosure provided herein, the skilled artisan would understand that the present invention is not limited in the number of molecules of interest that can be detected in a single multiplex reaction. That is, the design of unique sequences that can be detected and distinguished from the each other in a single reaction is well-known in the art. Further, one skilled in the art would appreciate, based upon the disclosure provided herein, that various technologies, such as, but not limited to, microchip arrays, slot blots, use of beacon probes, and other high-throughput assays allowing the processing of many samples, and providing the capability for multiplex assays, can be used in the methods of the present invention as exemplified herein, as known in the art, or using techniques to be developed in the future, the use of which can be readily contemplated based upon the disclosure provided herein. That is, current chip technology already provides that the number of antigens that can be assayed on a single chip exceeds the number of known red blood cell antigens. Further, where the cycling parameters of various PCR reactions are compatible, a single tube comprising numerous primer pairs can be used to multiplex the PCR reactions. Thus, multiplexing the reactions relating to the methods of the invention would appear to only be limited as to the number of spots on the chips, since the binding of phage to cells, the number of primers that can be used perform PCR in a single tube, and the like, do not limit the number molecules that can be assayed for using the methods of the invention.

The skilled artisan would understand, based upon the disclosure provided herein, that the invention encompasses amplification of the nucleic acid of interest (i.e., the nucleic acid contained by the bacteriophage expressing the antibody to the antigen-bearing moiety of interest which is bound to the cell by the specific binding of the antibody with its cognate antigen) using any method known in the art, as well as methods to be developed in the future. PCR amplification was discussed previously herein, and is exemplified elsewhere herein, as is IDAT, which is amplification of the nucleic acid using a transcription-based method. However, these are exemplary amplification methods only, and the present invention is not in any way limited to these, or any other, method for amplifying the nucleic acid contained by the phage of interest.

The invention also encompasses detecting the nucleic acid once it has been amplified. One skilled in the art would appreciate, once armed with the teachings provided herein, that any method for detection of a nucleic acid known in the art, or to be developed in the future, can be used to detect the nucleic acid in the method of the invention. Such detection methods include, but are not limited to, real-time PCR using fluorescent probes, detecting amplicons of the predicted size using size separation techniques (e.g., agarose gel electrophoresis), Southern and Northern blotting techniques, hybridization to oligonucleotide microarrays, and use of "molecular beacon" probes, discussed more fully elsewhere herein. Further, as more fully disclosed elsewhere herein, techniques to automate, accelerate, or otherwise improve the detection of the nucleic acid sequence of interest are contemplated. Such techniques include, but are not limited to, "electric field-accelerated hybridization to oligonucleotide microarrays" (Su et al., 2002, Electrophoresis 23:1551-1557), which provides rapid results, e.g., time from application of DNA (or RNA) to readout is less than about 10 minutes. Thus, techniques to improve the efficiency of the detection step are encompassed in the invention as would be understood by the skilled artisan.

B. Detection of Multiple Antigens

The present invention encompasses a method for detecting the presence of at least two different antigen-bearing moieties on a cell. The method comprises contacting at least two different bacteriophage, each encoding and expressing an antibody that specifically binds an antigen, where the two antibodies do not bind the same antigen. Any phage that are non-specifically bound with the cell are removed (e.g., by washing the cell), and the presence of any bound bacteriophage is detected by detecting the nucleic acid present in the phage. That is, are more fully described elsewhere herein, the sequence, or a portion thereof, of the nucleic acid present in the phage particle is exposed and the presence of the nucleic acid (i.e., the presence of its known nucleic acid sequence) is detected using methods well-known in the art. Because each bacteriophage comprises a nucleic acid sequence that is distinguishable from those present in other bacteriophages present in the same sample, the presence of various antigens can be detected in a single sample mixture. Such "multiplex" assays are not possible using antibody-based detection methods, since the reagents used to detect the presence of antibodies bound with the cell cannot readily distinguish between each antibody. Further, conventional blood typing does not use reagents that detect the presence of antibodies bound with the cell since many blood typing reagents, typically the decavalent IgMs, directly agglutinate the cells. In those assays, one cannot multiplex the reaction it would not be possible to determine which reagent caused the agglutination. However, methods based on detecting multiple, unique nucleic acid sequences, make assaying for various antigens, by detecting the nucleic acid sequences present within phage particles bound to/linked with those antigens via an antibody molecule expressed by the phage, possible as demonstrated herein.

One skilled in the art would appreciate, based upon the disclosure provided herein, that the various bacteriophage, each displaying a different antibody recognizing an antigen distinct from the antigens recognized by any other phage-displayed antibody present in the sample, can be contacted with the cell being assayed simultaneously, in the same reaction mixture. However, the bacteriophage can be contacted with the cell in serial fashion, such that each bacteriophage contacted with the cell, any unbound bacteriophage is removed, and the next bacteriophage can be contacted with the cell, the unbound phage removed, and on and on, until all of the bacteriophage have been allowed to bind with the cell such that all of the antigens of interest have been assayed for on the cell. All the bound phage can then be treated to release the nucleic acids present within, and the various nucleic acid sequences present in the sample can be detected as discussed more fully elsewhere herein. Because each bacteriophage expressing a unique antibody contains a nucleic acid comprising a known sequence that is distinct from the sequences of all the other bacteriophage nucleic acids used in the assay, the binding of each bacteriophage can be determined separately from all the others. Thus, the presence of each antigen assayed for can be determined by detecting the unique nucleic acid sequence associated with the bacteriophage displaying the antibody that bound with that antigen because detecting various nucleic acid sequences in a sample does not interfere with the detection of other, unrelated, sequences in that same sample.

The skilled artisan would appreciate, based upon the disclosure provided herein, that where speed is desired, different antigens can be assayed for in a single reaction mixture. Moreover, where greater sensitivity of the assay is desired, e.g., where forensic detection of a small sample is involved, or where the particular combination of phage required for the assay are somehow incompatible with the same amplification scheme or conditions, then the various reactions can be performed serially. Thus, while it is preferred that PCR be performed by adding all the relevant primers into one tube and amplifying all the fragments at once, the invention also encompasses methods where each antigen/ligand is identified in serial fashion using the same sample. In designing the primers and the stretches of phage(mid) DNA to amplify. it is therefore preferable to design specific sequences (tags) to be amplified in the phage DNA, rather than exploiting the difference in antibody or peptide sequence, since one can make them compatible in terms of multiplexing and cycling conditions. As exemplified herein for detection of B and Rh(D) antigens on an RBC using anti-B and anti-Rh(D) displayed by phage, the primers can be designed to be used in a single reaction and the phage were added together to the RBCs and the PCR was performed in a single tube to produce both 1100 bp and 1600 bp amplicons. While this is the preferred method, the invention is not limited to this particular scheme.

Therefore, a number of different phage-displayed antibodies (e.g., antibodies specific for various blood group antigens) can be contacted simultaneously with a sample of RBCs. The unbound phage are removed, and the nucleic acids of the phage bound with the cells are assayed to determine which phage bound with the cells. Since each bacteriophage contains a unique sequence "tag", nucleic acid methods can be used to determine which phage, and therefore, which antigens, are present on the cells. This "multiplex" method is a vast improvement over prior art methods which require that each antigen be assayed for separately, thereby requiring additional reagents, increasing the technical difficulty and length of the assay, and introducing more opportunity for errors in requiring additional steps and manipulations.

Accordingly, a number of different phage-displayed blood group antibodies can be contacted simultaneously to the same sample of red cells and the differences in antibody nucleotide sequence can be exploited to determine which ones bound and which ones did not, as demonstrated herein using anti B and anti-Rh(D) antibodies displayed on different phage. Such "multiplexing" is not possible by agglutination methods as one could never tell which antibody(ies) caused the agglutination.

That such a methodology is possible, i.e., that the simultaneous binding of multiple anti-RBC antibodies can be detected by the amplification and detection of antibody DNA, is demonstrated by the data disclosed herein where a model system comprising phage-displayed anti-blood group B and anti-Rh(D) human monoclonal antibodies was employed. However, the skilled artisan, based upon the disclosure provided herein, would readily appreciate that such "multiplexing" strategy is not limited to any particular antibodies, but can be used to detect multiple red blood cell antigens using a wide plethora of antibody-displaying phage, where each phage comprises a DNA sequence that can be detectably distinguished from the nucleic acid of other phage encoding antibodies having different specificities, or even phage encoding antibodies having the same specificities, so long as the nucleic acids of the phage can be distinguished from one another. Indeed, these methods are not limited to red blood cells or their antigens, but can be readily applied to any system where it is desirable to detect the presence of multiple antigens on a cell, or in a sample.

The skilled artisan would appreciate, as more fully discussed elsewhere herein, that where several antibody-displaying phage, each reactive with a different antigen of interest, can be used in a "multiplex" reaction where the antigens are detected in a single reaction, and/or within the same sample, the primers are selected such that the regions amplified by each primer pair (i.e., forward and reverse primers and, if desired, probe for the amplicon produced therefrom) are each distinguishable from each other.

C. Detection of Antibody in Serum

The present invention includes a method for detecting the presence of autoantibodies or alloantibodies in serum, more specifically, for detecting anti-red blood cell antibodies present in human serum (indirect antiglobulin test). The method comprises contacting a human red blood cell expressing at least one red blood cell antigen with a serum sample to be assayed. The cell is washed to remove non-specifically bound antibodies and the cell is then contacted with bacteriophage displaying an antiglobulin reagent on its surface. Where there is a human antibody (IgG, IgM, and the like) bound with the cell, the bacteriophage will bind via the antiglobulin reagent displayed by the phage. The presence of phage specifically bound with the cell (via binding with the human antibody on the cell) can then be detected as disclosed herein based on detection of a known nucleic acid sequence present in the bacteriophage. In this way, where the antigen composition of a panel of cells is known, this reference panel of cells can be used to assay for the presence of antibodies to these antigens in any sample by simply and rapidly detecting the nucleic acid of a bacteriophage displaying an antiglobulin on its surface, such that "phenotyping-by-genotyping" can be used to increase the efficiency and sensitivity, as well as to automate, assays that were previously performed using antibody-based detection methods.

D. Detection of Antibody or Complement Fragments on Red Blood Cells

The present invention includes a method for detecting the presence of autoantibodies, alloantibodies, or complement fragments bound to the surface of red blood cells, more specifically, for the diagnosis of autoimmune hemolytic anemia or for the determination of alloimmune destruction of transfused red blood cells (direct antiglobulin test). The method comprises washing a sample of red blood cells to remove non-specifically bound antibodies and then contacting the cells with bacteriophage displaying an antiglobulin reagent on its surface. Where there is human antibody or complement bound with the cell, the bacteriophage will bind via the antiglobulin reagent displayed by the phage. The presence of phage specifically bound with the cell (via binding with the human antibody or complement on the cell) can then be detected as disclosed herein based on detection of a known nucleic acid sequence present in the bacteriophage. In this way, "phenotyping-by-genotyping" can be used to increase the efficiency and sensitivity, as well as to automate, assays that were previously performed using antibody-based detection methods.

E. Performing Donor/Recipient Compatibility Testing

The present invention includes a method for assuring compatibility, i.e., non-reactivity, between antibodies in patient sera and an aliquot of red blood cells drawn from a unit of blood intended for transfusion (crossmatching). The method comprises contacting a sample of characterized donor red blood cells with a patient serum sample to be tested. The cells are washed to remove non-specifically bound antibodies and the cell is then contacted with bacteriophage displaying an antiglobulin reagent on its surface. Where there is human antibody bound with the cell, such as would be the case with an incompatible crossmatch, the bacteriophage will bind via the antiglobulin reagent displayed by the phage. The presence of phage specifically bound with the cell (via binding with the human antibody on the cell) can then be detected as disclosed herein based on detection of a known nucleic acid sequence present in the bacteriophage. In this way, "phenotyping-by-genotyping" can be used to increase the efficiency and sensitivity, as well as to automate, assays that were previously performed using antibody-based detection methods.

II. Kits

The invention includes various kits which comprise a compound, such as a bacteriophage displaying an antibody with known specificity for an antigen of interest, a primer pair for amplifying a known nucleic acid sequence present in the phage, a molecular beacon for detecting a known sequence present in the nucleic acid contained in the bacteriophage, a reagent for use in an IDAT reaction (e.g., T7 RNA polymerase, DNA polymerase I, dNTPs, and the like), and/or compositions of the invention, an applicator, and instructional materials which describe use of the compound to perform the methods of the invention, and any combination of the preceding components. Although exemplary kits are described below, the contents of other useful kits will be apparent to the skilled artisan in light of the present disclosure. Each of these kits is included within the invention.

In one aspect, the invention includes a kit for detecting the presence of an antigen-bearing moiety on a cell. The kit is used pursuant to the methods disclosed in the invention. Briefly, the kit may be used to contact a bacteriophage displaying an antibody that specifically binds with the antigen-bearing moiety when it is present on a cell. This is because, as more fully disclosed elsewhere herein, binding of the bacteriophage with the cell, and subsequent detection of a nucleic acid sequence known to be present in the phage, indicates that the phage bound with the cell, thereby indicating that the antibody displayed by the phage bound with its cognate antigen, thus, in turn, indicating that the antigen is present on the cell, thereby detecting the antigen by this novel "phenotyping-by-genotyping" method of the invention.

The kit further comprises an applicator useful for administering the bacteriophage, PCR primers, molecular beacons, and the like, to a sample. The particular applicator included in the kit will depend on, e.g., the method used to detect the antigen using "phenotyping-by-genotyping" as disclosed herein, and such applicators are well-known in the art and may include, among other things, a pipette, a syringe, a dropper, and the like. Moreover, the kit comprises an instructional material for the use of the kit. These instructions simply embody the disclosure provided herein.

In one aspect, the kit further comprises a bacteriophage expressing an antibody that specifically binds a red blood cell antigen, such as, but not limited to, RBC antigens A, B, Rh(D), Rh(C), Rh(c), Rh(E), Rh(e), K, $Fy^a$, $Fy^b$, M, N, S, s, $Jk^a$, $Jk^b$.

Further, in another aspect, the kit further comprises a molecular beacon probe wherein the nucleic acid sequence of the probe is complementary with a sequence such as, for instance, of the sequence of SEQ ID NO:3 and the sequence of SEQ ID NO:4, as exemplified herein. These sequences are contained within the nucleic acid contained by the bacteriophage such that sequences hybridizing therewith can detect the presence of phage(mid) nucleic acid. More specifically, the kit comprises a molecular beacon probe having a sequence such as, but not limited to, the sequence of SEQ ID NO:7, SEQ ID NO:8, SEQ ID NO:9, and SEQ ID NO:10.

In yet another aspect, the kit comprises a PCR primer than can amplify the nucleic acid sequence present in the phage. Such a PCR primer includes, but is not limited to, a primer comprising the sequence of SEQ ID NO:1 and the sequence of SEQ ID NO:2.

The kit includes a pharmaceutically-acceptable carrier. The composition is provided in an appropriate amount as set forth elsewhere herein.

Additional kits, such as those for detecting complement, and auto- and allo-antibodies in a sample, as well as kits for detecting any ligand of interest where a known ligand/receptor binding pair is known, are also included as would be readily appreciated by one skilled in the art based upon the disclosure provided herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Current technologies used in blood collection facilities, blood banks, and transfusion service laboratories are extraordinarily labor intensive, prone to human error, and an order of magnitude more expensive per test that those in other clinical laboratories. Coupled with a growing shortage of skilled medical technologists, dwindling supplies of human plasma-derived phenotyping reagents, and an inherent difficulty in fully automating 1950's-based agglutination methodologies, the ability to perform the hundreds of millions of pre-transfusion tests per year in a rapid, accurate, and cost-effective manner is a significant challenge.

The present invention relates to the development of novel molecular technologies and reagents pertinent thereto, to develop a new class of renewable, inexpensive, high-quality blood bank testing reagents that function in a rapid, high-throughput, automatable assay system.

A central feature of the novel technologies disclosed herein are red blood cell antigen-specific monoclonal antibodies displayed on the surface of bacteriophage particles. The naturally-occurring presence of unique DNA sequences within the phage particles has been exploited to develop an assay system in which the phenotype of a red cell is determined by assaying the genotype of the detecting reagent, i.e., the phage bearing an antibody that specifically binds with an antigen present on a red blood cell.

Such a strategy offers extraordinary sensitivity and specificity, requires minute amounts of testing materials and reagents, is easily adapted to automation, and is amenable to multiplexing strategies thereby offering the ability to perform simultaneous antigen profiling of a red cell sample in a single reaction vessel, all which offers substantial improvement over prior art methods.

A panel of phage-displayed antibody reagents specific for clinically-significant red cell antigens is developed using antibody phage display library technologies. Examples of these reagents and methodologies for their production have described previously (see, e.g., U.S. Pat. Nos. 5,876,925, and 6,255,455, both of which are incorporated by reference herein in their entirety), and are exemplified by the reagents used herein. These phage-display antibody reagents have been demonstrated to be superior to conventional blood bank reagents and can be used with all currently-available agglutination-based blood typing methods. Moreover, a novel blood typing platform based on this new generation of anti-red blood cell antibodies is disclosed, which novel platform makes full use of the coupled phenotypic/genotypic properties of these novel reagents.

Thus, the data disclosed herein demonstrates that the present invention overcomes several long-standing technical hurdles in the field of blood typing. The data disclosed herein demonstrate development of a new class of renewable, inexpensive, high-quality blood bank testing reagents and methodologies pertaining thereto, that function in a rapid, high-throughput, automatable assay system.

A feature of the novel technology disclosed herein are RBC antigen-specific monoclonal antibodies displayed on the surface of filamentous phage particles that are isolated using a number of technologies well-known in the art, and such technologies as are developed in the future. The phage particles physically link the phenotype of an antibody displayed on the phage (the antigen-binding moiety) with its genotype (the unique sequence of DNA within the particle that encodes the amino acid sequence of that particular antigen-binding moiety). Additionally, the phage particle can link the phenotype of the antibody displayed on its surface and the DNA present in the phage particle in that another portion of the DNA, which does not encode the antigen-binding portion of the molecule but which is associated therewith (i.e., a beacon sequence), can be detected such that detecting the identity of the antigen bound by the antibody displayed on the phage can be readily determined by detecting the presence of the beacon.

Thus, the naturally-occurring presence of unique DNA sequences within the particles has been exploited herein by developing a novel assay system in which the phenotype of an RBC being assayed is determined by assaying the genotype of the detecting reagent, i.e., the antibody-displaying phage and the DNA molecule encoding such antibody, or another unique DNA sequence (i.e., a beacon sequence) within the DNA contained by the phage. The rationale behind the development of this novel "phenotyping-by-reagent-genotyping" approach is the recognition that methodologies which use nucleic acid detection schemes offer the highest sensitivity and specificity, require minute amounts of testing materials and reagents, and are readily adaptable to automation.

Furthermore, nucleic acid-based assays are amenable to multiplexing strategies which, in the case of blood typing, would offer the possibility of simultaneously determining the antigen profile of a given RBC sample in a single reaction vessel. The ability to multiplex typing reactions using the technology proposed in this research application would represent a significant advantage for both blood collection facilities and transfusion services which historically have been limited to the conventional "one tube/one result" agglutination methodology. Therefore, the novel assays described herein allow the detection of multiple antigen-bearing moieties present on an RBC to be readily and quickly detected.

Phage-Display Technology

At the core of the proposed technology are RBC antigen-specific monoclonal antibodies which are displayed on the surface of filamentous bacteriophage particles (reviewed in Siegel, 2001, Transfusion Med. Rev. 15:35-52). In contrast to expensive and time-consuming conventional cellular methods for generating monoclonal antibodies from B-lymphocytes, antibody phage display works by immortalizing the immunoglobulin genes rather than the cells from which they were derived. By using molecular methods instead of cell transformation, "libraries" of phage particles are produced from populations of B-cells, each particle displaying a particular antibody specificity on the outside and containing the antibody's unique DNA sequence on the inside.

Methods for selecting phage particles specific to particular cell-surface antigens from such libraries have been described previously (e.g., Siegel et al., 1997, J. Immunol. Meth. 206: 73-85; U.S. Pat. No. 5,876,925, to Siegel) and hundreds of unique human anti-Rh(D) monoclonal phage-displayed antibodies have been produced to date (e.g., Siegel et al., 1997, J. Immunol. Meth. 206:73-85; Chang and Siegel, 1998, Blood 91:3066-3078; U.S. Pat. No. 6,255,455, to Siegel). Although monoclonal antibodies produced in this way can be expressed as soluble antibody molecules (unlinked to phage) that can agglutinate RBCs using the conventional indirect antiglobulin (i.e., Coombs) reaction (see Siegel and Silberstein, 1994, Blood 83:2334-2344), it has been established that the actual phage particles displaying the recombinant monoclonal antibodies can be used in agglutination reactions by substituting anti-M13 phage antibody for the Coombs reagent (Siegel et al., 1997, J. Immunol. Meth. 206:73-85; U.S. Pat. No. 5,985, 543, to Siegel). An advantage of this method in agglutination assays using intact phage displaying the antibody is increased sensitivity since as few as approximately 10 anti-Rh(D)-expressing phage particles (compare with about 150-1000 conventional IgG) are needed to induce agglutination due to the greater degree of crosslinking by anti-M13 afforded by the relatively large size (approximately 0.5 microns) of the particles.

More importantly, for commercial application, is the ability of such phage-displayed antibodies to direct their own replication within $E.\ coli$, allowing enough reagent to be produced for use in conventional red cell typing of nearly 500,000 units of blood for a reagent cost of a few dollars (see Siegel et al., 1997, J. Immunol. Meth. 206:73-85).

The substitution of conventional blood bank typing reagents with phage-displayed recombinant antibodies in agglutination assays is a vast improvement over prior art Coombs-based agglutination methodologies in and of itself for the reasons stated above—the ability to clone human antibodies without the need to B-cell transformation, greater assay sensitivity, inexpensive production in bacterial culture, and others (Siegel, 2001, Transfusion Med. Rev. 15:35-52). However, the data disclosed herein demonstrate the further dramatic improvement upon the phage-based technology by exploiting the naturally-occurring presence of unique DNA sequences contained within the antibody-expressing phage particles to facilitate high-throughput automation and multiple-antigen typing in a single reaction vessel (multiplexing). The method of the invention can comprise the various steps illustrated in FIG. 1, and is more fully disclosed elsewhere herein.

Using antibody phage-display and other technologies available in the art, a set of novel monoclonal reagents specific for clinically-significant RBC antigens can be cloned, produced, and the performance characteristics thereof can be validate according to the teachings provided herein, as well as methods known in the art and to be developed in the future. For instance, previous studies demonstrated the production and isolation of such reagents with specificities for RBC antigens B, anti-Rh(D), M and N (see, e.g., Chang and Siegel, 2001, Transfusion. 41:6-12; Siegel et al., 1997, J. Immunol. Meth. 206:73-85; Chang and Siegel, 1998, Blood 91:3066-3078; Czerwinski et al., 1995, Transfusion. 35:137-144; Czerwinski et al., 1999, Transfusion. 39:364-371). Such methods can be applied to develop, among others, anti-A, anti-Rh(C, c, E, e), as well as antibodies in the Kell, Duffy, Kidd, and Ss blood groups. These reagents can be used in conventional manual and automated agglutination assays, as well as in the novel methods disclosed herein.

An index set of anti-blood group B and anti-Rh(D) phage was produced and unique DNA sequence tags (i.e., beacon sequences), oligonucleotide primer and hybridization sites, and polymerase promoters are inserted into the DNA that codes for each antibody. The performance characteristics of a number of nucleic acid amplification/detection schemes is assessed to identify and quantify the RBC binding of each reagent as exemplified herein using group B and anti-Rh(D) phage reagents.

The data disclosed herein demonstrate that polymerase chain reaction (PCR) and agarose gel electrophoresis can be used to simultaneously detect and differentiate the binding of two different anti-RBC antibody specificities. These data demonstrate that screening using these methods can be performed rapidly, and can be scaled, and automated for commercial application.

Amplification of Phage DNA Using the Polymerase Chain Reaction:

In one aspect, the binding of a RBC-specific phage-displayed antibody, e.g., a phage particle expressing anti-Rh(D), was detected through the addition of oligonucleotide primers specific to the anti-Rh(D)'s nucleic acid sequence exposed when, for example, the bound phage particles were heated to denature the phage coat. One primer can be complementary to a generic sequence contained in the phage DNA (irrespective of antibody specificity) and the other primer can be complementary to, e.g., a sequence specific to that phage, such as, but not limited to, the CDR3 hypervariable region of the antibody's heavy chain (i.e., the sequence that is unique for a given antibody). The measurement of the resultant amplified antibody DNA can indicate the presence of that antibody's cognate antigen on the surface of a cell being examined. Without wishing to be bound by any particular theory, a number of different phage-displayed blood group antibodies can be contacted simultaneously to the same sample of red cells and the differences in antibody nucleotide sequence can be exploited to determine which ones bound and which ones did not as demonstrated herein using anti B and anti-Rh(D) antibodies displayed on different phage. Such "multiplexing" is not possible by agglutination methods as one could never tell which antibody(ies) caused the agglutination.

That such a methodology is possible, i.e. that the simultaneous binding of multiple anti-RBC antibodies can be detected by the amplification and detection of antibody DNA, is demonstrated by the data disclosed herein where a model system comprising phage-displayed anti-blood group B and anti-Rh(D) human monoclonal antibodies was employed. However, the skilled artisan, based upon the disclosure provided herein, would readily appreciate that such "multiplexing" strategy is not limited to any particular antibodies, but can be used to detect multiple red blood cell antigens using a wide plethora of antibody-displaying phage, where each phage comprises a DNA sequence that can be detectably distinguished from the nucleic acid of other phage encoding antibodies having different specificities, or even phage encoding antibodies having the same specificities, so long as the nucleic acids of the phage can be distinguished from one another. Using PCR and agarose gel electrophoresis to amplify and then detect unique coding sequences within each type of phage particle based on, e.g., size of the amplicons, the data disclosed herein demonstrate that a sample of RBCs was simultaneously phenotyped for B and Rh(D) with extraordinary sensitivity. That is, the single assay detected the equivalent of 20 attograms of conventional IgG and required 10,000-fold fewer RBCs (135 picoL or about 1500 total RBCs) than a conventional agglutination reaction.

In practice, however, a rapid, scaleable, and automatable DNA readout can be used instead of agarose gel electrophoresis. Many methods are well-known in the art, and several such methods are discussed more fully elsewhere herein. Nonetheless, the skilled artisan would understand, once armed with the teachings of the invention, that a wide plethora of methods to detect nucleic acids can be used in the methods of the invention, and the invention is not in any way limited to the methods exemplified and discussed herein.

Amplification of Phage DNA Using Transcription-Mediated Amplification

In addition to using PCR for phage DNA amplification step (step B in FIG. 1), methods based on detection of transcription of phage antibody DNA, instead of its amplification, can be used in the methods of the invention. More specifically, immunodetection by this method has been used to detect the binding of antibodies to which oligonucleotides containing the T7 RNA polymerase promoter site have been chemically-conjugated with glutaraldehyde as described in Zhang et al. (2001, Proc. Natl. Acad. Sci. USA 98:5497-5502). This technique for the transcription of DNA that is attached in vivo to an antibody by virtue of its physical association in phage particles can be used as an alternative to PCR and other amplification techniques. This technology has been termed IDAT, which stands for immuno-detection amplified by T7 RNA (Zhang et al., 2001, Proc. Natl. Acad. Sci. USA 98:5497-5502). By placing the T7 RNA polymerase promoter site upstream from an arbitrary sequence tag in the phagemid DNA, the addition of T7 RNA polymerase and NTPs rapidly (100 bases per second) produces tag transcripts through the consecutive and progressive binding of T7 enzymes to their promoter.

Since T7 RNA polymerase binding to RNA products does not occur, amplification is linear not exponential as in PCR. For RBC phenotyping, such linear amplification provides an advantage over PCR (and certainly over conventional agglutination methods) in that quantitative information (i.e., relative antigen copy number per cell) about multiple antigens can be determined simultaneously from a single sample of cells. An example, among others, of where such quantification can be useful in blood banking is the detection of "weak Rh(D)" phenotypes as reviewed in Mollison et al. (1997, In: Blood Transfusion in Clinical Medicine, 10th ed., Blackwell Scientific Publications, Oxford, England).

An additional advantage of transcription-based detection methods, such as, but not limited to, IDAT, over PCR is elimination of temperature cycling once the antibody phage DNA is released from the particles. Elimination of temperature cycling reactions simplify instrument design and lowers cost of the assay. Nevertheless, PCR and transcription methods each have advantages and disadvantages that are well-known in the art such that the skilled artisan can readily determine which method, or any other method, can be used for any particular assay and the conditions desired therefor. This is because PCR, transcription, and many other methods to detect a nucleic acid, can be used successfully in the methods of the present invention and the skilled artisan would appreciate what method to employ based on art-recognized factors.

Detection of Phase DNA Using Molecular Beacons:

Molecular beacons are stem-and-loop-structured oligonucleotides with a fluorescent label at the 5' end and a universal quencher at the 3' end (see, e.g., Tyagi and Kramer, 1996, Nature Biotech. 14:303-308; Broude, 2002, Trends in Biotechnology 20:249-256). When the stem is closed (in the absence of complementary nucleic acid), the fluorophore and quencher are in close proximity and fluorescent energy is absorbed by the quencher and fluorescence is quenched and not detectable. In the presence of complementary nucleic acid, the loop of the beacon hybridizes and the fluorophore and quencher separate such that quenching does not occur. Photons are then emitted from the fluorophore, unquenched, at the wavelength specific for that fluorophore and fluorescence is then detectable. By combining a number of beacons in one tube, each with a different fluorophore at their 5' ends, multiple DNA (Tyagi et al, 1998, Nature Biotech. 16:49-53) or RNA (de Baar et al., 2001, J. Clin. Microbiol. 39:1895-1902) targets can be simultaneously detected by measuring the spectrum of colors emitted from the reaction vessel.

Molecular beacons of two different colors are incorporated into the PCR and transcription reactions to detect the presence of antibody-specific DNA. As described elsewhere herein, anti-Rh(D) and anti-B phage DNA are modified to contain short DNA sequences that can be amplified (or transcribed) and subsequently detected using molecular beacons as described elsewhere herein. The design an production of such "beacon" sequences, and nucleic acid sequences comprising sequences "complementary" thereto are well known in the art. Indeed, software programs are commercially available to assist in the design of such sequences, including the molecular beacon probe sequences complementary to a sequence of interest.

Figure 4A:
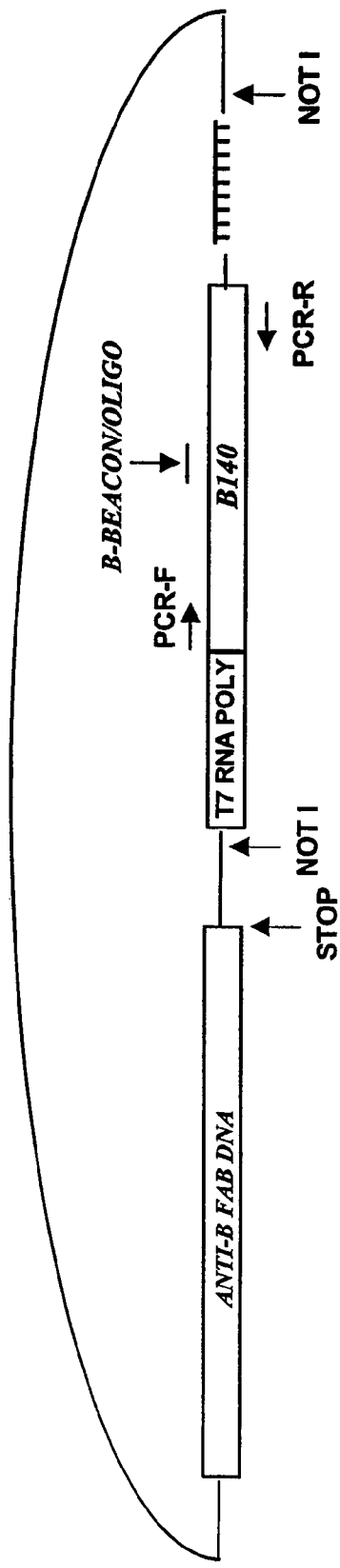
FIGS. 4A and 4B, depict a diagram illustrating various phagemid constructs for anti-B-expressing phage particles (FIG. 4A) and anti-Rh(D)-expressing phage particles (FIG. 4B). The diagram illustrates cloning of inserts of about 140 basepairs in size (more specifically, 142 bp) into the anti-B phagemid ("B140") or anti-Rh(D) phagemid ("D140") downstream of the 20-bp T7 RNA polymerase promoter site. The 142-bp inserts are identical except for an internal 33-bp region to which B- or Rh(D)-specific molecular beacons or microarrayed oligos hybridize ("B-Beacon/Oligo" and "D-Beacon/Oligo", respectively). B140 and D140 can be amplified by PCR with an identical set of oligonucleotide primers ("PCR-F" and "PCR-R") or transcribed using T7 RNA polymerase. The sequence of the "B 140" insert is 5'-TGCTATGTCACTTCCCCTTGGTTCTCT-CATCTGGCCTGGTGCAATAGGCCCTGC ATGCACTG-GATGCACTCTATCCCATTCTGCAGCTTC-CTCATTGATGGTCTCTTT TAACATTTGCATGGCTGCTTGATGTCCCCCCACT-3' (SEQ ID NO:3) and the sequence of the "D140" insert is 5'-TGCTATGTCACTTCCCCTTGGTTCTCT-CATCTGGCCTGGTGCAATAGGCCCTGC ATGCACTG-GATGCACTCTGTTTTACCTCATTATCCT-TCTGCCAGCGCTAGCTTT TAACATTTGCATGGCTGCTTGATGTCCCCCCACT-3' (SEQ ID NO:4). The forward PCR primer ("PCR-F") is: 5'-TGCTATGTCACTTCCCCTTGGTTCTCT-3' (SEQ ID NO:5) and the reverse PCR primer ("PCR-R") sequence is: 5-AGTGGGGGGACATCAAGCAGCCATGCAAAT-3' (SEQ ID NO:6). The B-Beacon and D-Beacon sequences are as follows, showing the fluorescent derivatives and the stem structures in lower case. The "B-Beacon" sequence is as follows: 6-FAM-gcgagcATCCCATTCTGCAGCTTCCT-CATTGATGGTCTCgctcgc-DABCYL (SEQ ID NO:7. The "D-Beacon" is: TAMRA-cgagcGTTTTACCTCATTATCCT-TCTGCCAGCGCTAGCgctcgc-DABCYL (SEQ ID NO:8). The upper case letters in the beacon sequences represent the respective sequences in B140 and D140 to which the beacons anneal. Therefore, the upper case letters are the sequences of the oligonucleotides that are used for the DNA array detection. That is, a B-oligo is: 5'-ATCCCATTCTGCAGCTTC-CTCATTGATGGTCTC-3' (SEQ ID NO:9), and a "D-oligo" is: 5'-GTTTTACCTCATTATCCTTCTGCCAGCGCTAGC-3' (SEQ ID NO:10).
Figure 4B:
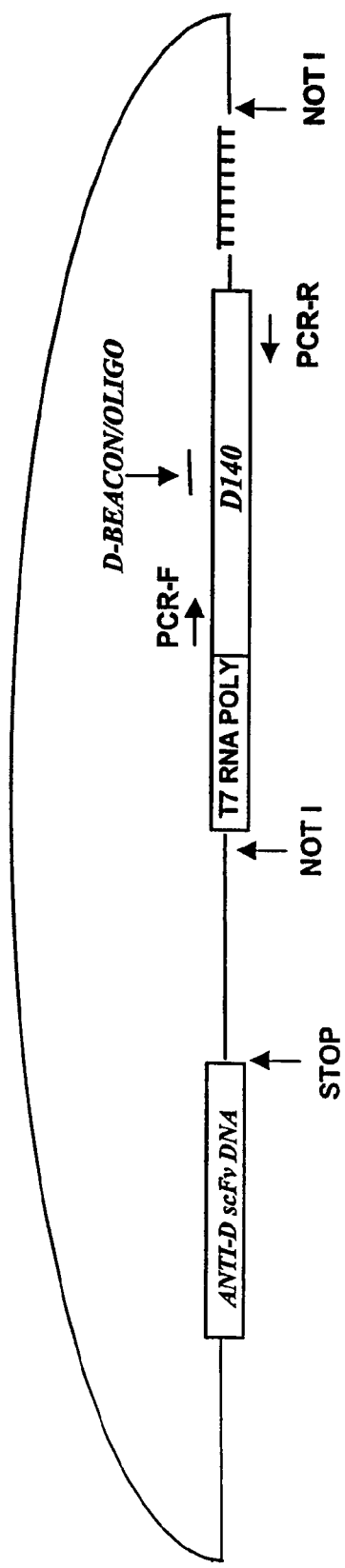

Further, such beacons and sequences that bind therewith, such as those exemplified in FIG. 4, comprise the following sequences: the sequence of the "B140" insert is 5'-TGCTAT-GTCACTTCCCCTTGGTTCTCTCATCTG-GCCTGGTGCAATAGGCCCTGC ATGCACTGGATG-CACTCTATCCATTCTGCAGCTTCCTCATTGATGGTC TCTTT TAACATTTGCATGGCTGCTTGATGTC-CCCCCACT-3' (SEQ ID NO:3) and the sequence of the "D140" insert is 5'-TGCTATGTCACTTCCCCTTGGT-TCTCTCATCTGGCCTGGTGCAATAGGCCCTGC ATG-CACTGGATGCACTCTGTTTTACCTCAT-TATCCTTCTGCCAGCGCTAGCTTT TAACATTTGCATGGCTGCTTGATGTCCCCCCACT-3' (SEQ ID NO:4). The forward PCR primer ("PCR-F") is: 5'-TGCTATGTCACTTCCCCTTGGTTCTCT-3' (SEQ ID NO:5) and the reverse PCR primer ("PCR-R") sequence is: 5-AGTGGGGGGACATCAAGCAGCCATGCAAAT-3' (SEQ ID NO:6). The B-Beacon and D-Beacon sequences are as follows, showing the fluorescent derivatives at the ends and the stem structures in lower case letters. The "B-Beacon" sequence is as follows: 6-FAM-gcgagcATCCCATTCTG-CAGCTTCCTCATTGATGGTCTCgctcgc-DABCYL (SEQ ID NO:7. The "D-Beacon" is: TAMRA-cgagcGTTTTACCT-CATTATCCTTCTGCCAGCGCTAGCgctcgc-DABCYL (SEQ ID NO:8). The upper case letters in the beacon sequences represent the respective sequences in B140 and D140 to which the beacons anneal. Therefore, the upper case letters are the sequences of the oligonucleotides that are used for the DNA array detection. That is, a "B-oligo" is: 5'-ATC-CCATTCTGCAGCTTCCTCATTGATGGTCTC-3' (SEQ ID NO:9), and a "D-oligo" is: 5'-GTTTTACCTCATTATC-CTTCTGCCAGCGCTAGC-3' (SEQ ID NO:10).

The present invention is not limited to these exemplary sequences; rather, the invention encompasses such additional sequences as can be readily designed by the skilled artisan once armed with the disclosure provided herein. That is, the design and use of beacon sequences are well-known in the art and are not discussed further herein and the sequences disclosed herein are merely an example of the sequences that can be used to practice the invention. For instance, many fluorescer-quencher pairs are known in the art, including, but not limited to, those exemplified herein which encompass 6-carboxyfluorescein (6-FAM), 6-carboxytetramethylrhodamine (TAMRA), and DABCYL (a non-fluorescent chromophore that serves as a universal quencher for any fluorophore in a molecular beacon: 4-(4-dimethylaminophenylazo)-benzoic acid). Such molecules are well known in the art, and are described in, e.g., U.S. Pat. Nos. 6,395,517, and 6,615,063, and are not discussed further herein.

Detection of Phage DNA Using Oligonucleotide Microarrays:

In addition to molecular beacons, hybridization of fluorescent RBC phage antibody amplicons (from PCR) or transcripts (produced using IDAT) to arrays of complementary oligonucleotide probes can be used to indirectly quantify the amount (if any) of bound antibody in a sample. Further, although the use of conventional methods for hybridization to such microarrays are diffusion limited and may require several hours to obtain adequate fluorescent signals, this process can be accelerated by 2-3 orders of magnitude through the application of an electric field across the surface of an inexpensive indium tin oxide-coated glass slide as described in Su et al. (2002, Electrophoresis 23:1551-1557). This process, known in the art as "electric field-accelerated hybridization to oligonucleotide microarrays" provides rapid results, e.g., time from application of DNA (or RNA) to readout is less than about 10 minutes. Therefore, electric field-accelerated hybridization can be used to further enhance the rapid detection of antigens of interest present on a cell (e.g., a red blood cell, a platelet, and the like).

The present invention is not limited to blood typing, but has wide potential uses in many other areas of transfusion medicine, such as, but not limited to, platelet antigen testing, and has broad application in transplantation immunology (HLA antigen typing) and particularly forensic medicine, where multiplexing of reactions can provide the most amount of information from minute amounts of testing samples. In addition, the construction of antiglobulin reagents (e.g., anti-IgG, -IgM, -C3 complement component) expressed on phage particles can be used to perform serum screening for pre-formed anti-RBC antibodies, reverse group typing, or to perform direct/indirect Coombs tests using a methodology that detects the antiglobulin reagents' associated DNA. The antiglobulin phage reagents can be isolated from immune murine phage display libraries, or through the cloning of pre-existing hybridoma immunoglobulin mRNA using techniques well-known in the art.

Anti-Blood Group B and Anti-Rh(D) Typing Using Phase DNA Analysis

The data disclosed herein demonstrate detection of anti-blood group B and anti-Rh(D) antigens on RBCs using the novel methods of the invention. That is, two phage displayed human monoclonal antibodies—an anti-blood group B and an anti-Rh(D)—both previously isolated from the panning of phage display libraries constructed from immunized individuals (Chang and Siegel, 2001, Transfusion. 41:6-12; Siegel et al., 1997, J. Immunol. Meth. 206:73-85) were used demonstrating the multiplexing detection of these two antigens.

Figure 2:
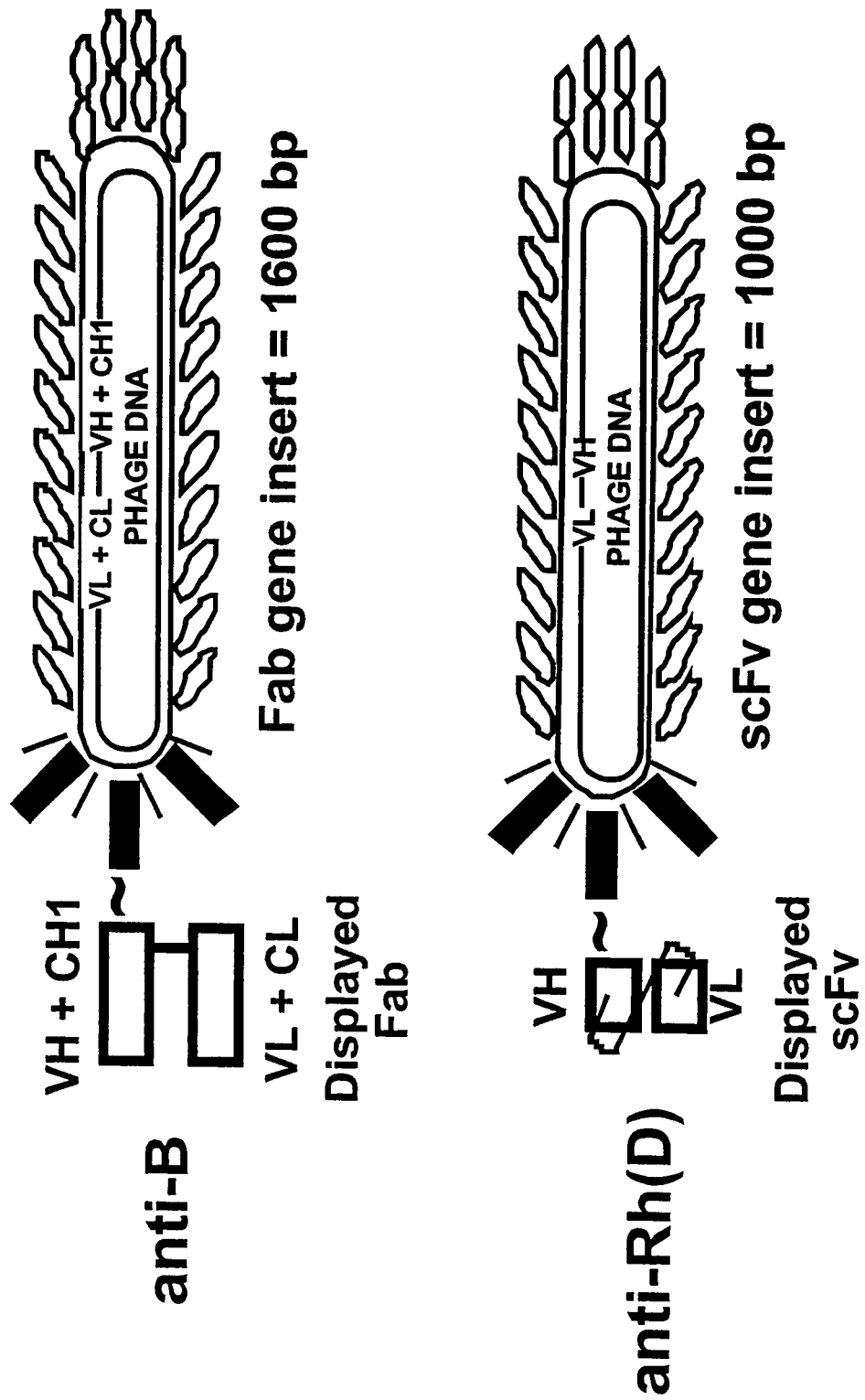
FIG. 2 is a diagram of a schematic representation of anti-B (top) and anti-Rh(D) (bottom) phage-displayed human monoclonal RBC antibodies.

For the purposes of this study, one antibody (the anti-B termed FB5.7) was expressed as a phage displayed Fab fragment and the other (the anti-Rh(D), termed E1 M2) as a single-chain Fv (scFv) fragment (FIG. 2). These antibodies were described previously in Chang and Siegel, 2001, Transfusion. 41:6-12; Siegel et al., 1997, J. Immunol. Meth. 206:73-85; Chang and Siegel, 1998, Blood 91:3066-3078; and U.S. Pat. No. 5,876,925, No. 5,985,543, and No. 6,255,455, all to Siegel. These data demonstrate that various antibody forms (e.g., Fab, scFv, and the like) can be readily used in the methods of the invention.

PCR amplification of the antibody coding regions of the corresponding phagemid DNA was predicted to produce products of different lengths (i.e., 1600 bp and 1000 bp) and agarose gel electrophoresis was then be used to genetically determine the presence of anti-B and/or anti-Rh(D) antibodies instead of conventional antibody-based detection methods based on the different sizes of the predicted amplicons.

Before performing binding assays of the phage displayed reagents with RBCs, a series of PCR reactions with serial dilutions of the anti-B or anti-Rh(D) phage preparations were performed to validate the novel genetic detection method and to determine its sensitivity. PCR of the phagemid antibody coding regions produced the predicted product sizes of 1600 bp for the anti-B-encoding Fab DNA and 1000 bp for the anti-Rh(D)-encoding scFv DNA. Remarkably, the sensitivity of detection when visualizing only 10% of the total PCR reaction products, was about 100 phage antibody particles. This value represents the equivalent of only $1.7 \times 10^{-22}$ moles or approximately $2 \times 10^{-17}$ g of IgG (about 20 attograms), a startling level of sensitivity not reached by previous methods for blood typing.

For PCR amplification of the inserts, the forward primer ("5-prime LC") was as follows: 5'-AAGACAGCTATCGC-GATTG-3' (SEQ ID NO:1); and the reverse primer ("GBACK") was as follows: 5'-GCCCCCTTATT-AGCGTTTGCCATC-3' (SEQ ID NO:2).

Figure 3:
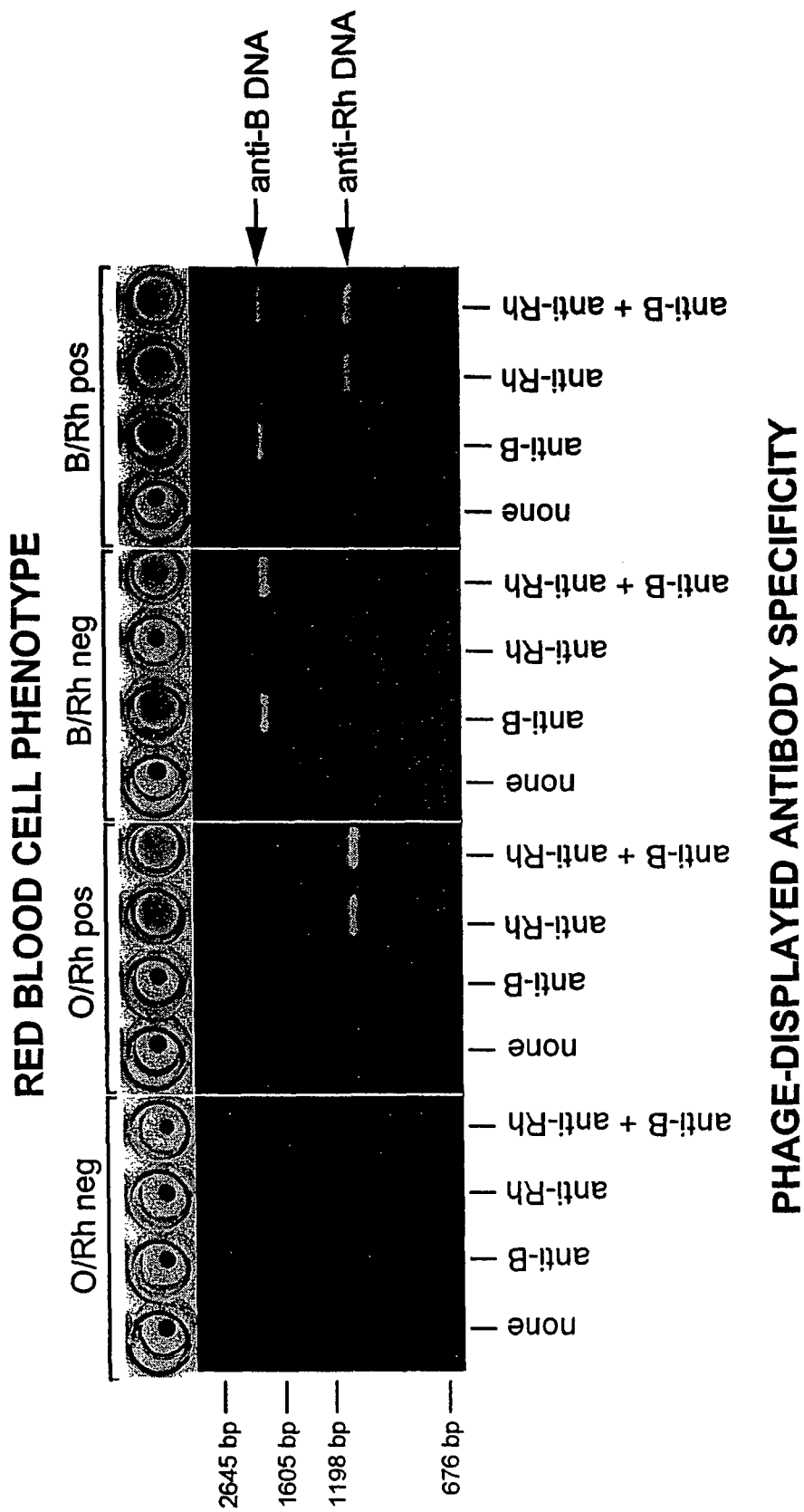
FIG. 3 is an image depicting phenotyping RBCs for the blood group B and Rh(D) antibodies in a multiplex phage antibody assay. Four possible RBC phenotypes (positive or negative for the blood group B antigen and positive or negative for the Rh(D) antigen) were incubated with phage displayed anti-B alone, anti-Rh(D) alone, anti-B and anti-Rh(D) together, or buffer. After washing away unbound phage reagent, RBCs were resuspended in anti-M13 phage antibody, an aliquot of the cell suspension was removed, diluted 200-fold in water, and 2-microliters of the diluted phage/lysed RBCs were subjected to PCR. The balance of the anti-M13 resuspended RBC samples were placed in microtiter plate wells and assayed for agglutination as described elsewhere herein (e.g., Siegel et al., 1997, J. Immunol. Meth. 206:73-85). Note that agglutination (top panel, wells with large crosslinked cell pellets) only occurs with the appropriate antibody/cell phenotype combination as expected. Most notably, only the appropriate antibody sequence was detected (1600-bp product with RBCs that expressed blood group B antigen; 1000-bp product with RBCs that expressed the Rh(D) antigen) and there was no detectable background (i.e., no anti-B DNA product with type O RBCs which do not express group A or B antigens; and no anti-Rh(D) DNA product was detected using Rh(D)-negative cells). For PCR amplification of the inserts, the forward primer ("5-prime LC") was as follows: 5'-AAGACAGCTATCGCGATTG-3' (SEQ ID NO:1); and the reverse primer ("GBACK") was as follows: 5'-GCCCCCTTATTAGCGTTTGCCATC-3' (SEQ ID NO:2).

To determine whether this genetic assay of using anti-B and anti-Rh(D) phage-displayed antibodies could be used to correctly phenotype RBCs, an experiment was performed, which demonstrated perfect concordance between the known phenotypes of the reagent RBCs, the conventional agglutination-based test results performed using the phage antibodies, and the novel genetic testing method results (FIG. 3). Therefore, the data disclosed herein demonstrate the effectiveness of the novel "phenotyping-by-reagent genotyping" as well as the ability to multiplex phenotype determinations.

Furthermore, using the PCR protocol disclosed herein, the assay is remarkably sensitive given that the results shown in the lanes of the agarose gel depicted in FIG. 3 represent only 10% of the total reaction product, and the number of RBCs added to each PCR reaction was only about 1500, or the equivalent of 135 picoL of RBCs. In contrast, conventional methods utilize approximately 10,000 times more RBCs per agglutination assay.

Development of Phage-Displayed Anti-RBC Typing Reagents

The methods utilized to clone, produce, and validate the performance characteristics of phage-displayed anti-RBC monoclonal antibodies have been the focus of numerous publications (e.g., Siegel, 2002, In: Methods in Molecular Biology: Antibody Phage Display: Methods and Protocols, vol. 178, pp. 219-226, Aitkem & O'Brien, eds., Humana Press, Totowa, N.J.; Siegel, 2000, In: Phage Display of Proteins and Peptides: A Laboratory Manual, vol. 23, pp. 23.21-23.32, Cold Spring Harbor Press, Cold Spring Harbor, N.Y.; Siegel and Chang, 1997, In: Antibody Engineering: New Technologies, Applications, & Commercialization, IBC, Boston, Mass.), as well as several issued U.S. patents (see, supra). Specimens (residual peripheral blood, spleen tissue, bone marrow, and the like) from which RBC antigen specificities other than B, Rh(D), M, and N were isolated, have already been archived using residual diagnostic patient material.

Rapid and Scaleable Phage Antibody Detection Methodology

The phagemid DNA of anti-RBC blood group, e.g., anti-B and anti-Rh(D), antibodies are modified such that the phage antibodies each contain a unique tag that can be amplified by PCR or transcribed by T7 RNA polymerase and subsequently detected by a corresponding pair of unique molecular beacons or microarrayed oligonucleotides. The tags are inserted in the phagemid DNA outside of the anti-B or anti-Rh(D) coding region so as not to disrupt antibody expression and display on the phage coat (see, e.g., FIG. 4). A selected number of nucleic acid amplification/detection schemes are performed using the modified set of anti-RBC phage-displayed antibodies in order to assess the performance characteristics in order to maximize the efficiency of rapid, multiplexed, RBC phenotyping.

For the modification of phagemid DNA, B140 and D140 were sequenced. PCR-F and PCR-R, along with B-Beacon/Oligo in kinetic PCR (molecular beacon) assays to measure the level of HIV gag cDNA (O'Doherty et al., 2000, J. Virol. 74:10074-10080) have been performed. B140 and D140 are ligated into anti-B or anti-Rh(D) phagemids using standard cloning techniques. Antibody-expressing phage particles are produced from their modified DNAs and their binding properties are validated as described previously (Chang and Siegel, 1998, Blood 91:3066-3078; Siegel, 2002, In: Methods in Molecular Biology: Antibody Phage Display: Methods and Protocols, vol. 178, pp. 219-226, Aitkem & O'Brien, eds., Humana Press, Totowa, N.J.; Siegel, 2000, In: Phage Display of Proteins and Peptides: A Laboratory Manual, vol. 23, pp. 23.21-23.32, Cold Spring Harbor Press, Cold Spring Harbor, N.Y.; Siegel and Chang, 1997, In: Antibody Engineering: New Technologies, Applications, & Commercialization, IBC, Boston, Mass.).

Amplification of phage DNA by PCR experiments are performed on RBC/phage-incubated samples as described previously elsewhere herein, except for use of ABI 7700 spectrofluorimetric thermal cycler, addition of one or both of B-BEACON or D-BEACON, or use of PCR fluorescein labeling mix (dNTPs spiked with fluorescein dUTP) depending on detection method. For amplification of phage DNA by transcription a series of experiments analogous to those performed using PCR are performed using the following RNA amplification procedure: Phage particles are heated to 94° C. for 2 minutes to denature the phage coat and release the single-stranded phagemid DNA. Since T7 RNA polymerase requires double-stranded DNA as template, DNA polymerase I, dNTPs, and the Not I-containing reverse primer used for cloning D140/B140 are used to synthesize second-strand DNA during RNA synthesis. To initiate RNA amplification, amplification buffer containing T7 RNA polymerase (Zhang et al., 2001, Proc. Natl. Acad. Sci. USA 98:5497-5502) is added in the presence of one or both molecular beacons or fluorescein-12-UTP depending on the detection method as described below.

For the detection of amplified phage DNA using molecular beacons, B-Beacon (FAM-labeled) and D-Beacon (TAMRA-labeled) stem-and-loop structures are present both singly and in combination during PCR amplicon formation and during RNA transcription. The shortest time-to-positivity (fewest PCR cycles/shortest time for RNA transcription), where positivity is at least 2 logs of fluorescence above background, is determined. Initially, sensitivity assays are performed using serial dilutions of phage and followed by binding experiments using antigen-negative and positive RBCs. The ability to multiplex reactions with anti-B and anti-Rh(D) is assessed and titering numerous variables are examined including relative concentrations of each beacon, amount of inputted phage antibodies, number of RBCs, time of RBC/phage incubation, and number of washes. In addition, the effect on the fluorescent signal as a function of antigen copy number per RBC is assessed (e.g., compare Rh(D) phenotypes $R_2R_2$, $R_1R_1$, $R_1r$, $D^w$, partial Rh(D), and the like.) (Mollison et al., 1997, In: Blood Transfusion in Clinical Medicine, 10th ed., Blackwell Scientific Publications, Oxford, England) and quantification of antigen density with exponential (PCR) and linear (transcription) amplification are compared.

For the detection of amplified phage DNA on electric-field enhanced oligonucleotide microarrays, oligonucleotides corresponding to the hybridizing nucleotides of B-Beacon and D-Beacon are synthesized and applied to indium tin oxide-coated glass slides using an arrayer. Slides are processed, incubated with fluorescently-labeled PCR amplicons or RNA transcripts, and washed as described (Su et al., 2002, Electrophoresis 23:1551-1557) and analyzed using a ScanArray 5000 microarray scanner.

Similar to the approach taken in the molecular beacon experiments described above, the detection of anti-B- and -Rh(D)-associated phage DNA in the shortest time is optimized by varying similar parameters. Because RBCs with and without each antigen are included, test samples with one or both (or neither) phage antibody, and a microarray with multiple spots, a number of internal positive and negative controls are present that will permit an accurate assessment of signal/noise ratio. Based on previous experience, it is estimated that less than 10 minutes from the time of sample application to hybridization and readout are required.

Routine molecular cloning methods are used and troubleshooting is straightforward. Furthermore, it is unlikely that there is any adverse affect on antibody expression or display resulting from the introduction of B140/D140. Other nucleotide sequences have been successfully cloned into the Not I site of pComb3X without any untoward effects. Furthermore, there are other convenient unique restriction sites into which B140/D140 (or an alternative set of tags) can be cloned, if necessary or desired. The important features of the assays is the relative time-to-positivity for the amplification/detection strategy used and it lends itself to multiplexing of RBC phenotyping. PCR studies disclosed herein demonstrated sensitivity and specificity. The transcription procedure, although linear, offers the simplicity of isothermal amplification reactions and, with an input of $10^7$-$10^9$ template DNAs per sample, sensitivity will likely not be a limiting factor. Indeed, previous studies utilizing transcription methods with glutaraldehyde-conjugated oligonucleotide/monoclonal antibodies demonstrated $10^9$ to $10^{11}$-fold greater sensitivity than ELISA assays and enhanced chemiluminescence-Western blot assays, respectively, with a reported ability to detect as little as a few copies of antigen in a cell lysate (Zhang et al., 2001, Proc. Natl. Acad. Sci. USA 98:5497-5502).

Further, the methods disclosed herein present vast improvement over instruments, such as, but not limited to, the Olympus™ PK7200 automated analyzer, which are considered state-of-the-art for a device that uses hemagglutination technology. This is because with a reported throughput of several hundred specimens per hour, the methods disclosed herein represent feasible and ultimately superior in that time-to-positivity (including RBC/phage incubation times) is in the 30-minute range, reactions take place in a 96-well format, and multiple antigen determinations (multiplexing) can take place in a single well.

Detection of Auto- and Alloantibodies in Serum

This assay is performed in a manner similar to the standard indirect antiglobulin test (see, e.g., Mollison, 1997, In: Blood Transfusion in Clinical Medicine, 10th ed., Blackwell Scientific Publications, Oxford, England) with the substitution of antiglobulin expressing phage particles for the conventional antiglobulin reagent, and the detection of bound phage reagent as disclosed herein based on detection of a known nucleic acid sequence present in the bacteriophage. Briefly, members of a panel of reagent red blood cells of known antigen composition are each incubated with an aliquot of patient sera. Cells are washed to remove non-specifically bound antibodies and the cells are then contacted with bacteriophage displaying an antiglobulin reagent. The antiglobulin reagent can be specific for all human immunoglobulin isotypes if desired, or specific for only one class such as IgM or IgG. Using algorithms well known in the field of immunohematology, the specificity or specificities of anti-red blood cell antibodies present in the patient sera is determined based on the pattern of reactivity of sera with panel red blood cells.

Detection of Antibody or Complement Fragments on Red Blood Cells

This assay is performed in a manner similar to the standard direct antiglobulin test (see, e.g., Mollison, 1997, Blood Transfusion in Clinical Medicine, 10th ed., Blackwell Scientific Publications, Oxford, England) with the substitution of antiglobulin expressing phage particles for the conventional antiglobulin reagent, and the detection of bound phage reagent as disclosed herein based on detection of a known nucleic acid sequence present in the bacteriophage. Briefly, a sample of red blood cells is washed to remove non-specifically bound antibodies and then contacted with bacteriophage displaying an antiglobulin reagent on its surface. The antiglobulin reagent preparation can comprise molecules specific for IgG, for complement C3d, or both (e.g., anti-IgG antibody, anti-C3d antibody, both, and the like). Where there is human antibody or complement bound with the cell, the bacteriophage binds via the antiglobulin reagent displayed by the phage. The presence of phage specifically bound with the cell (via binding with the human antibody or complement on the cell) is then detected as disclosed herein based on detection of a known nucleic acid sequence present in the bacteriophage.

Performing Donor/Recipient Compatibility Testing

This assay is performed in a manner similar to the standard Coombs crossmatch test (see, e.g., Mollison, 1997, In: Blood Transfusion in Clinical Medicine, 10th ed., Blackwell Scientific Publications, Oxford, England) with the substitution of antiglobulin expressing phage particles for the conventional antiglobulin reagent, and the detection of bound phage reagent as disclosed herein based on detection of a known nucleic acid sequence present in the bacteriophage. Briefly, the method comprises contacting a sample of donor red blood cells with a patient serum sample. The cells are washed to remove non-specifically bound antibodies and the cell is then contacted with bacteriophage displaying an antiglobulin reagent (e.g., anti-IgM or anti-IgG) on its surface. Where there is human antibody bound with the cell, such as would be the case with an incompatible crossmatch, the bacteriophage binds via the antiglobulin reagent displayed by the phage. The presence of phage specifically bound with the cell (via binding with the human antibody on the cell) is detected as disclosed herein based on detection of a known nucleic acid sequence present in the bacteriophage.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of detecting the presence of a known antigen-bearing moiety on a cell, said method consisting the steps of: 1) antigen detection, 2) amplification of phage nucleic acid, and 3) detection of phage nucleic acid,
wherein said antigen detection step consists of:
a) contacting a cell with a bacteriophage expressing an antibody known to specifically bind with said antigen-bearing moiety wherein said bacteriophage comprises a nucleic acid, wherein the sequence of said nucleic acid is known and wherein at least a portion of the sequence of said nucleic acid is correlated to the phenotype of said antigen-bearing moiety;
b) denaturing any of said bacteriophage specifically bound with said cell to release said nucleic acid;
wherein said amplification step consists of amplifying said known nucleic acid to generate an amplified product; and
wherein said detection of phage nucleic acid step consists of detecting said amplified product, wherein detecting said amplified product detects the presence and phenotype of said antigen-bearing moiety on said cell.

2. The method of claim 1, wherein said steps are performed in a single reaction vessel.

3. The method of claim 1, said method further consisting washing said cell between said antigen detection step and said amplification of phage nucleic acid step.

4. The method of claim 1, wherein said cell is a red blood cell and said antigen-bearing moiety is a red blood cell antigen.

5. The method of claim 4, wherein said red blood cell antigen is selected from the group consisting of A, B, Rh(D), Rh(C), Rh(c), Rh(E), Rh(e), K, $Fy^a$, $Fy^b$, M, N, S, s, $Jk^a$, and $Jk^b$.

6. The method of claim 1, wherein said cell is a white blood cell and wherein said antigen-bearing moiety is selected from the group consisting of a lymphocyte antigen, a monocyte antigen, and a granulocyte antigen.

7. The method of claim 1, wherein said cell is a platelet and further wherein said antigen-bearing moiety is a platelet antigen.

8. The method of claim 7, wherein said platelet antigen is selected from the group consisting of HPA-1a, HPA-1b, HPA-2a, HPA-2b, HPA-3a, HPA-3b, HPA-4a, HPA-4b, HPA-5a, HPA-5b, HPA-6b, HPA-7b, HPA-8b, HPA-9b, HPA-10b, $Gov^a$, and $Gov^b$.

9. The method of claim 1, wherein said nucleic acid comprises a sequence complementary to a molecular beacon probe, wherein said sequence does not encode said antibody.

10. The method of claim 9, wherein said sequence is complementary to a sequence selected from the group consisting of the sequence of SEQ ID NO:3 and the sequence of SEQ ID NO:4.

11. The method of claim 10, wherein the sequence of said molecular beacon probe is selected from the group consisting of the sequence of SEQ ID NO:7, the sequence of SEQ ID NO:8, the sequence of SEQ ID NO:9, and the sequence of SEQ ID NO:10.

12. The method of claim 9, wherein said molecular beacon probe comprises a fluorophore.

13. The method of claim 1, wherein said nucleic acid is amplified using polymerase chain reaction (PCR).

14. The method of claim 13, wherein said PCR comprises using a primer selected from the group consisting of the sequence of SEQ ID NO:1 and the sequence of SEQ ID NO:2.

15. The method of claim 1, wherein said nucleic acid is amplified by transcription using immuno-detection amplified by T7 RNA (IDAT).

16. A method of detecting the presence of at least two known different antigen-bearing moieties on a cell, said method comprising the steps of 1) antigen detection, 2) amplification of phage nucleic acid, and 3) detection of phage nucleic acid,
wherein said antigen detection step consists of:
a) contacting a cell with a first bacteriophage expressing an antibody known to specifically bind with a first antigen-bearing moiety wherein said first bacteriophage comprises a first nucleic acid, wherein the sequence of said first nucleic acid is known and wherein at least a portion of the sequence of said first nucleic acid is correlated to the phenotype of said first antigen-bearing moiety;
b) contacting said cell with a second bacteriophage expressing an antibody known to specifically bind with a second antigen-bearing moiety wherein said second bacteriophage comprises a second nucleic acid, wherein the sequence of second said nucleic acid is known and wherein at least a portion of the sequence of said second nucleic acid is correlated to the phenotype of said second antigen-bearing moiety, and wherein the sequence of said first nucleic acid is detectably different from the sequence of said second nucleic acid;
wherein said amplification step consists of amplifying said first nucleic acid to generate a first amplified product; and amplifying said second nucleic acid primer to generate a second amplified product; and
wherein said detection of phage nucleic acid step consists of detecting the binding of said first bacteriophage with said antigen-bearing moiety by detecting the presence of said first amplified product, wherein detecting said first amplified product detects the presence and phenotype of said first antigen-bearing moiety on said cell; and
detecting the binding of said second bacteriophage with said antigen-bearing moiety by detecting the presence of said second amplified product, wherein detecting said second amplified product detects the presence and phenotype of said second antigen-bearing moiety on said cell.

17. A method of detecting the presence of a known anti-red blood cell antibody in human serum, said method consists of,
a) contacting a human red blood cell expressing at least one human red blood cell antigen on the surface of said cell with said serum;
b) washing said cell to remove any antibody bound non-specifically with said cell;
c) contacting said cell with a bacteriophage expressing an anti-humanglobulin reagent wherein said bacteriophage comprises a nucleic acid, wherein the sequence of said nucleic acid is known and wherein at least a portion of said nucleic acid is correlated to the phenotype of said anti-red blood cell antibody;
d) denaturing any of said bacteriophage specifically bound with said cell to release said nucleic acid; and
e) amplifying said released nucleic acid to generate an amplified product and detecting said amplified product, wherein detecting said amplified product detects the presence and phenotype of said anti-red blood cell antibody in said serum.

18. The method of claim 17, wherein said anti-human-globulin reagent is selected from the group consisting of an anti-human IgG, an anti-human IgM, an anti-human kappa/lambda light chain antibody, a staphylococcal Protein A, a streptococcal Protein G, and a peptostreptococcal Protein L.

19. The method of claim 17, wherein said steps (c) through (e) are performed in a single reaction vessel.

20. The method of claim 17, wherein said antibody is selected from the group consisting of an autoantibody and an alloantibody.

21. A method of detecting the presence of a known anti-red blood cell autoantibody in a human, said method consists of,
a) obtaining a red blood cell from said human;
b) washing said cell to remove any antibody bound non-specifically with said cell;
c) contacting said cell with a bacteriophage expressing an anti-humanglobulin reagent wherein said bacteriophage comprises a nucleic acid, wherein the sequence of said nucleic acid is known and wherein at least a portion of said nucleic acid is correlated to the phenotype of said anti-red blood cell autoantibody;
d) denaturing any of said bacteriophage specifically bound with said cell to release said nucleic acid; and
e) amplifying said released nucleic acid to generate an amplified product and detecting said amplified product, wherein detecting said amplified product detects the presence and phenotype of said anti-red blood cell autoantibody in said human.

22. The method of claim 21, wherein said steps (c) through (e) are performed in a single reaction vessel.

23. A method of detecting the presence of a known ligand in a sample, said method comprising the steps of: 1) antigen detection, 2) amplification of phage nucleic acid, and 3) detection of phage nucleic acid,
wherein said antigen detection step consists of:
a) contacting a cell with a bacteriophage expressing a receptor known to specifically bind with said ligand wherein said bacteriophage comprises a nucleic acid, wherein the sequence of said nucleic acid is known and wherein at least a portion of said nucleic acid is correlated to the phenotype of said ligand;
b) denaturing any of said bacteriophage specifically bound with said cell to release said known nucleic acid;
wherein said amplification step consists of amplifying said known nucleic acid to generate an amplified product; and
wherein said detection of phage nucleic acid step consists of detecting said nucleic acid, wherein detecting said nucleic acid detects the presence and phenotype of said ligand in said sample.

24. The method of claim 23, wherein said ligand is present on a cell.

25. The method of claim 23, wherein said sample is a biological sample obtained from a human.

26. The method of claim 25, wherein said biological sample is a cell sample.

27. The method of claim 26, wherein said cell sample comprises a red blood cell and wherein said ligand is a red blood cell antigen and further wherein said receptor is an antibody.

28. The method of claim 23, wherein said steps are performed in a single reaction vessel.

* * * * *